United States Patent [19]

Boswell, Jr. et al.

[11] 3,950,329

[45] Apr. 13, 1976

[54] FLUORINATED CEPHALOSPORINS

[75] Inventors: George Albert Boswell, Jr.; David R. Brittelli, both of Wilmington, Del.; William J. Middleton, Chadds Ford, Pa.

[73] Assignee: E. I. Du Pont de Nemours and Company, Wilmington, Del.

[22] Filed: Dec. 11, 1972

[21] Appl. No.: 314,023

[52] U.S. Cl............ 260/243 C; 424/246; 260/239.1
[51] Int. Cl.²....................................... C07D 501/20
[58] Field of Search ............................... 260/243 C

[56] References Cited

UNITED STATES PATENTS

| | | | |
|---|---|---|---|
| 3,544,581 | 12/1970 | Essery | 260/243 C |
| 3,705,892 | 12/1972 | Cooper | 260/243 C |
| 3,705,897 | 12/1972 | Murphy | 260/243 C |

OTHER PUBLICATIONS

Von Halasz et al., Chem. Ber. 104 1247 (1971).

*Primary Examiner*—Nicholas S. Rizzo
*Attorney, Agent, or Firm*—Anthony P. Mentis

[57] ABSTRACT

Cephalosporins having a fluorine atom on the 3-methyl carbon are active antibiotics.

12 Claims, No Drawings

FLUORINATED CEPHALOSPORINS

BACKGROUND OF THE INVENTION

1. Field of the Invention

This invention relates to novel compounds having the cephem nucleus and a fluorine on the methyl side chain at the 3-position and a novel method for the preparation of such compounds having up to 2 fluorines at this position.

2. Description of the Prior Art

In general, cephalosporins are antibiotics related to penicillin except that the cephalosporins are often effective against penicillin resistant organisms. They have drawbacks however in having lower oral absorption and lower activity and various attempts have been made to improve these properties through chemical modification of the cephalosporin molecule.

The cephalosporin C nucleus can be named as 1-aza-5-thia-6R-bicyclo[4,2,0]octan-8-one, although cepham or cephem (for $\Delta^2$ or $\Delta^3$-unsaturate) is simpler and easier to use for the compounds. The structure of cephalosporanic acid is

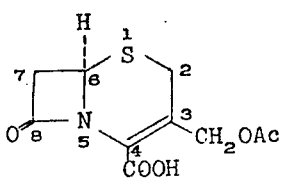

A halogen derivative, 3-bromomethyl (prepared by N-bromosuccinimide on 3-methyl cephem) has been proposed in South African Pat. No. 6900,761. Other recently issued patents such as Netherlands Pat. No. 7,004,479 and French Pat. No. 1,589,109 disclose 3-halomethyl derivatives where the halogen is specified as Cl, Br or I. Recent West German Pat. No. 2,052,531 appears to disclose the monofluoro derivative but does not give any method of fluorine-containing reagents whereby such monofluoro derivative would be obtainable. It is widely recognized that properties and synthetic methods for preparing fluoro compounds are quite different than for the other halogens. No mention is made in the art of polyhalo derivatives, much less the difluoromethyl compound.

The cephalosporin ring system includes a β-lactam ring fused to nitrogen of a thiazine ring system. Some of these ring systems are unstable to hydrolysis and fluorination conditions. Furthermore polyhalogen derivatives are generally hydrolytically unstable and it is not surprising that in this field of antibiotic transformations no processes have been suggested for fluorination of cephalosporins.

DESCRIPTION OF THE INVENTION

The invention embraces a fluorinated cephalosporin compound of the formula:

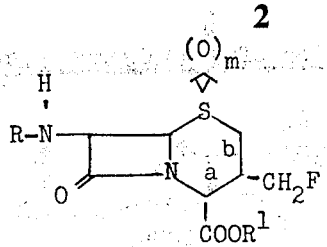 wherein $m$ is a zero or 1;
$a$ and $b$ are either a single or double bond with the proviso that $b$ is a double bond only when $m = 0$ and $a$ is a single bond;
R is H or

in which Q has up to 8 carbon atoms and is hydrocarbyl, amino substituted hydrocarbyl or heterocyclic group; and
$R^1$ is H, hydrocarbyl of up to 13 carbon atoms or polychloro hydrocarbyl, alkali metal, alkaline earth metal, ammonium or amine salt.

It is to be understood that when "$a$" is a single bond and "$b$" is a double bond, there is a hydrogen atom on each of the number 2 and 4 carbon atoms in the ring. When "$a$" is a double bond and "$b$" is a single bond there are two hydrogens on the 2 carbon atom.

The invention also includes pharmaceutically acceptable acid addition salts of the compounds where, for example, R is H. Such salts include the hydrochloride, sulfate, nitrate, phosphate, acetate, tartrate and citrate, etc.

Specific examples of Q are 2-thienylmethyl, 3-[1,2,5-thiadiazolyl]methyl, phenylmethyl, 3-[2,5,6-tricyanopyrazinyl]methyl and furfurylmethyl. Examples of $R^1$ are diphenylmethyl and 2,2,2-trichloroethyl as well as hydrogen; alkali metal, e.g., sodium or potassium; alkaline earth, e.g., calcium; ammonium or amine salts, e.g., trimethylammonium, N-methylpiperidine, etc.

The new process of this invention includes the fluorination by a fluorinating reagent of the formula $R^3SR_3$ where $R^3$ is a diprimaryalkylamino group, the alkyls having up to 4 carbon atoms, under anhydrous conditions of cephalosporins containining in the 3-position either a hydroxymethyl or aldehyde group. The reaction is generally conducted under relatively mild conditions, e.g., from −80° to +75°C., preferably 0 to 35°C. whereby oxygen of the 3-oxy- or oxo-methyl group is replaced by fluorine without substantial reaction with other oxygen groups in the cephalosporin. When the starting material contains a 3-hydroxymethyl group, the fluorination process yields a compound where $R^3$ is $CH_2F$. When the starting material contains a 3-aldehyde group, the fluorination process yields a compound where $R^3$ is $CHF_2$.

The diprimaryalkylaminosulfur trifluorides are known compounds. In general they are prepared by the reaction of a dialkylaminotrimethylsilane with sulfur tetrafluoride at a low temperature in an inert solvent, see Halasz, et al., Chem. Ber. 103, 594–602 (1970). Examples are dimethylaminosulfur trifluoride, diethylaminosulfur trifluoride, dipropylaminosulfur trifluoride and dibutylaminosulfur trifluoride.

The following sections show the sequence of steps useful in producing the compounds.

A. Preparation of 3-fluoromethylcephems
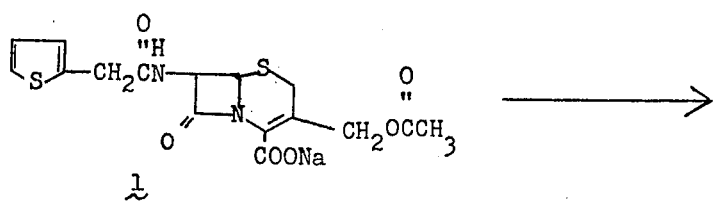
1
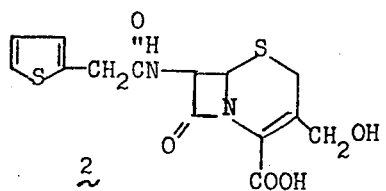
2
2 →
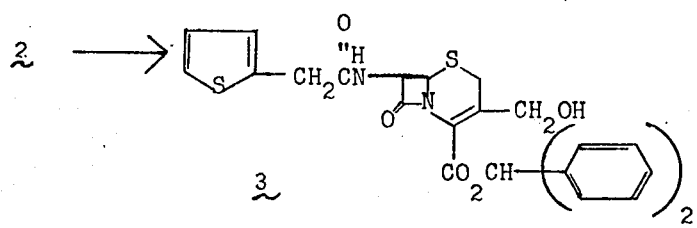
3
3 →
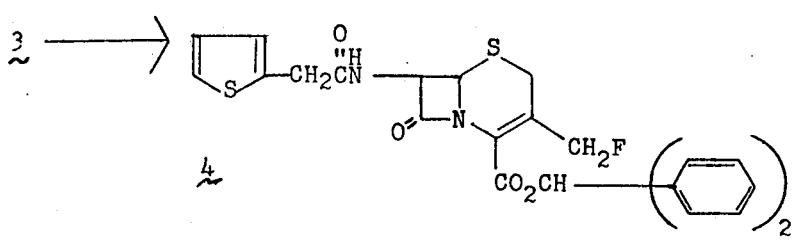
4
4 →
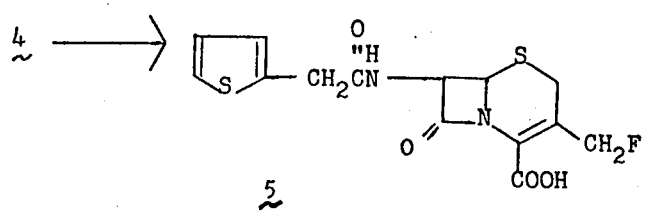
5
3 →
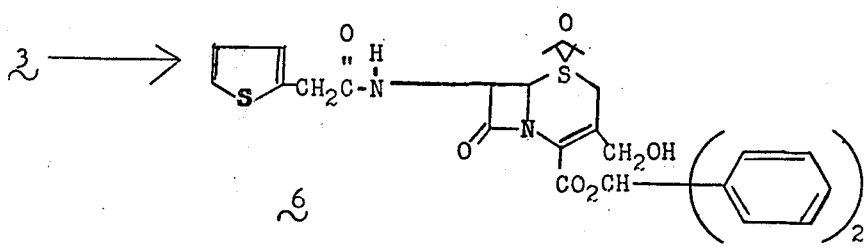
6
6 →
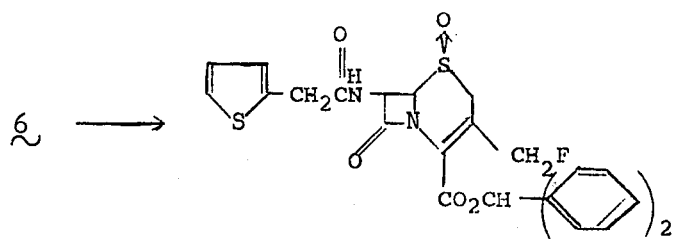
7

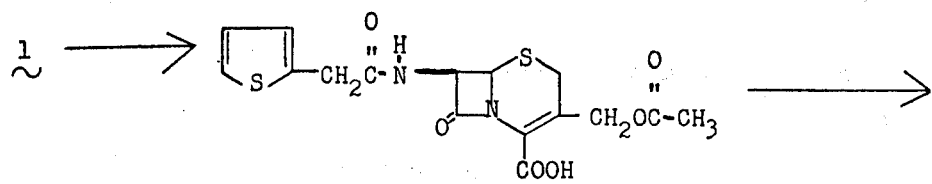
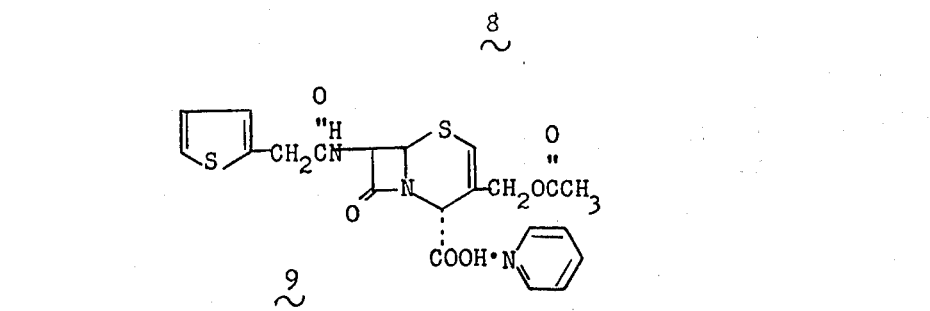
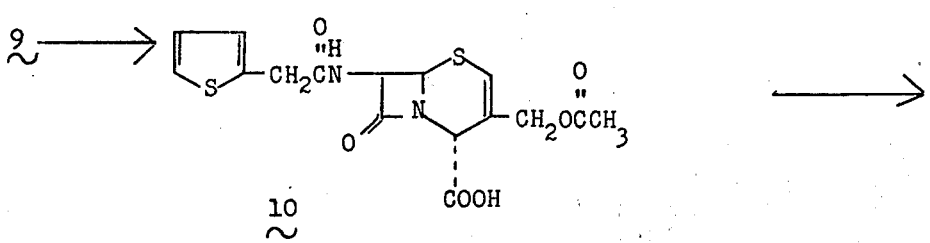
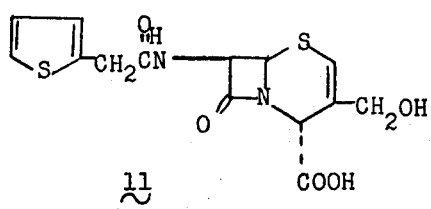
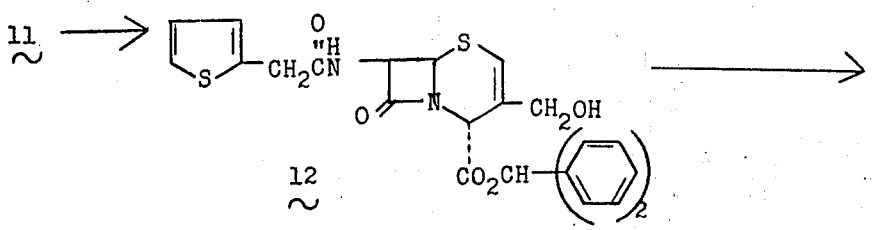
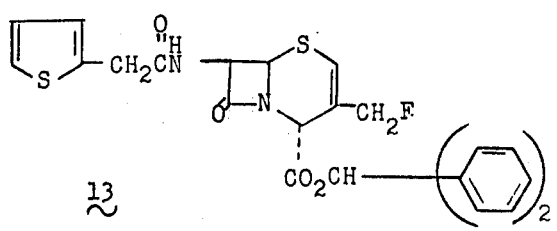

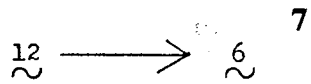
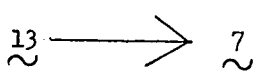
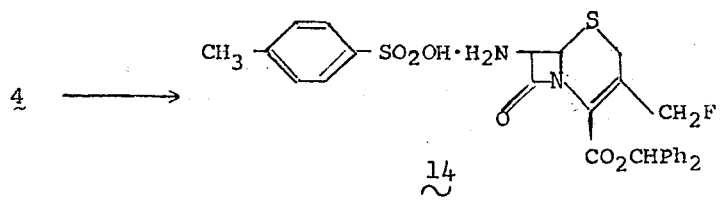
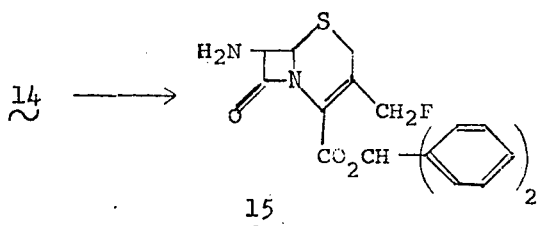
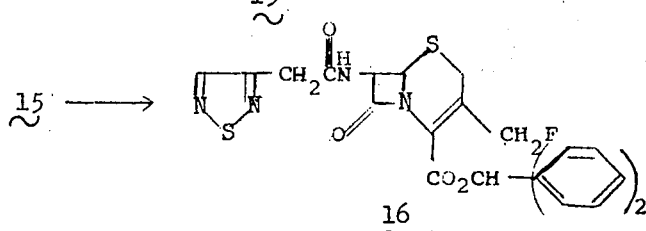
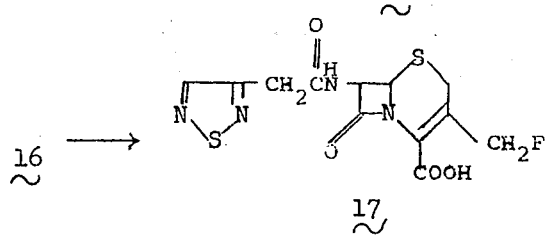
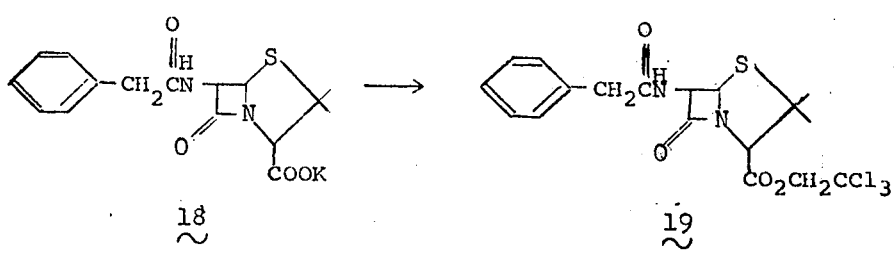
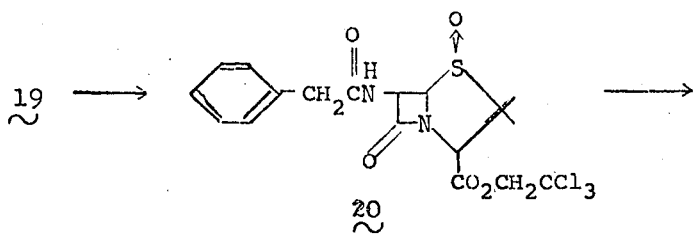
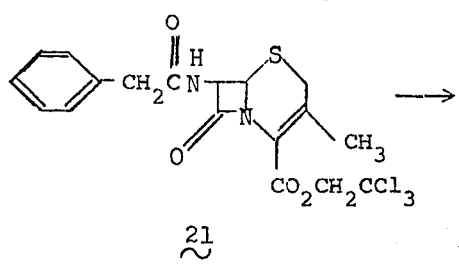

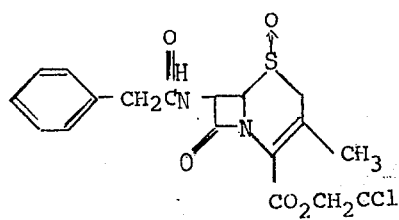
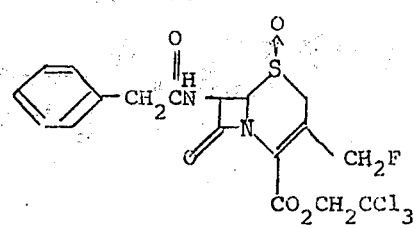
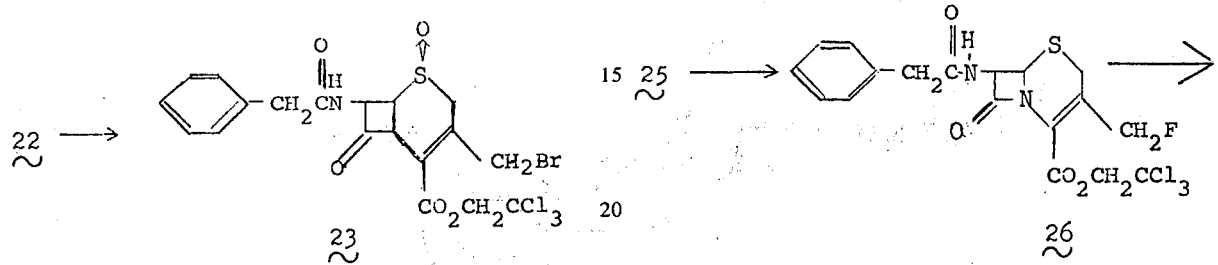
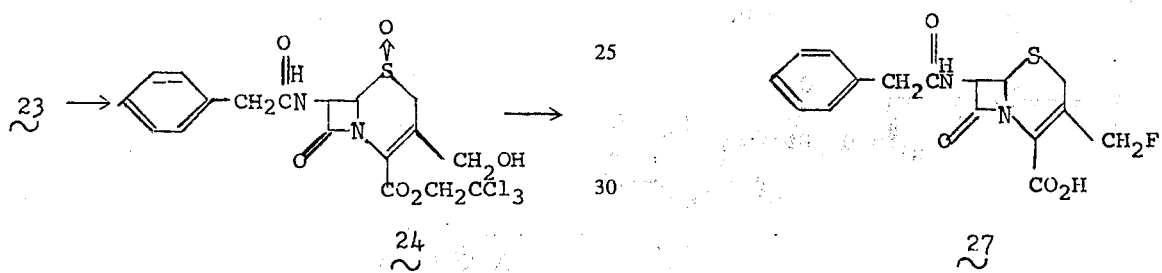
B. Preparation of 3-difluoromethylcephems
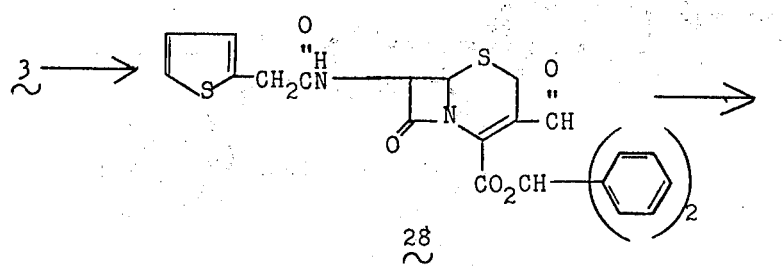
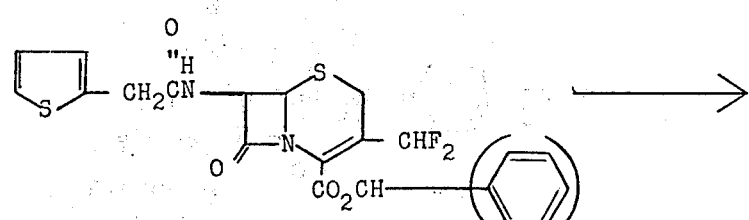
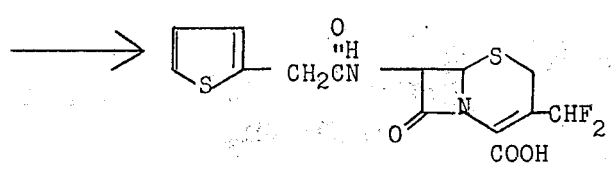

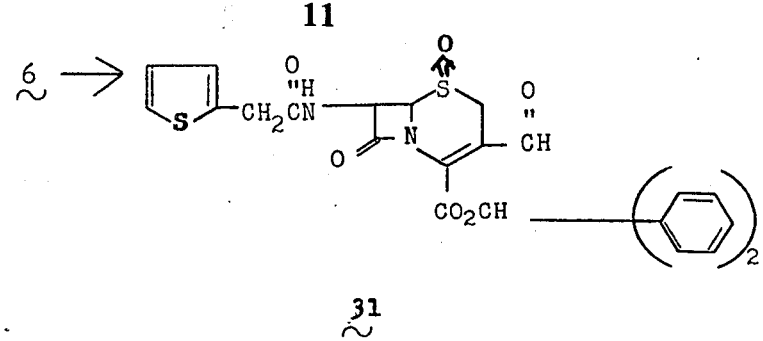
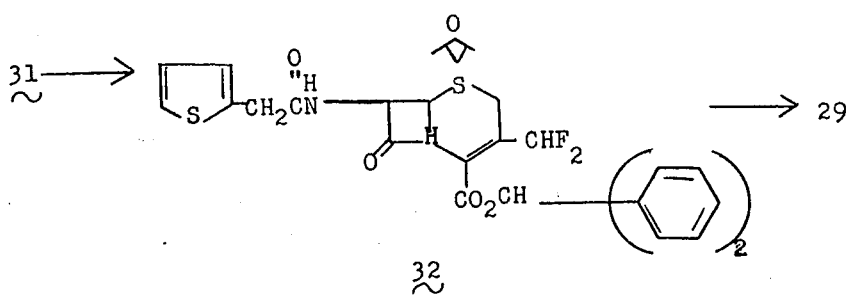
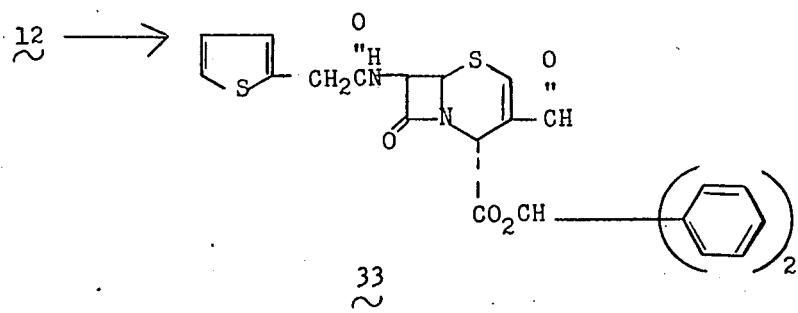
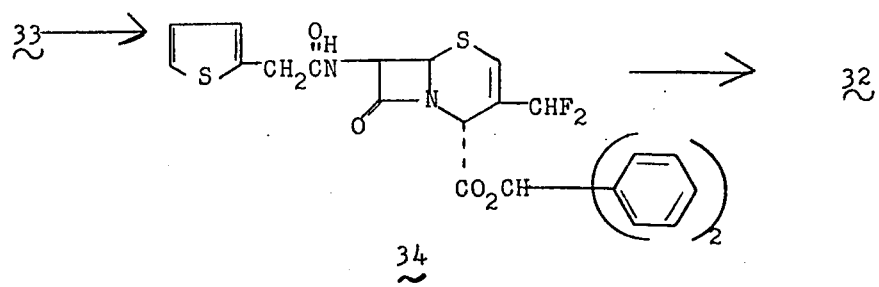
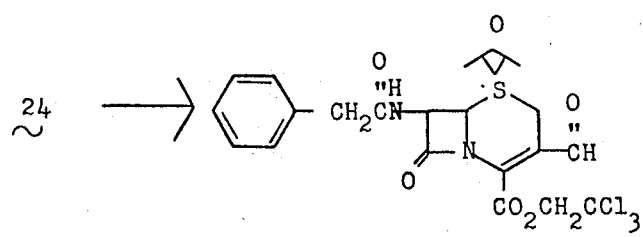
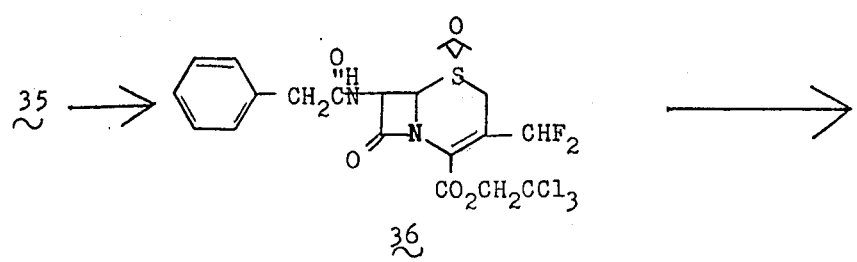

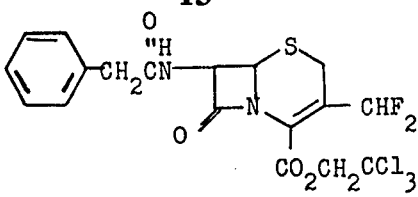

37

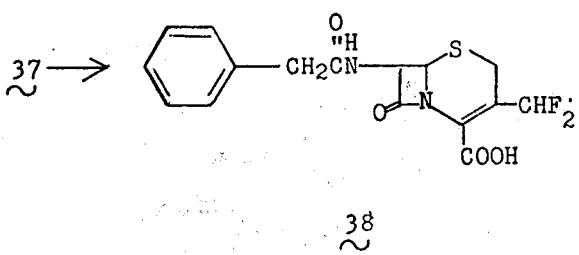

38

SPECIFIC EMBODIMENTS OF THE INVENTION

In the illustrative examples below all temperatures are Centigrade and all parts are by weight unless otherwise stated.

EXAMPLE 1

A1. Preparation of 3-Hydroxymethyl-7-(2-thienylacetamido)-3-cephem-4-carboxylic acid (2).

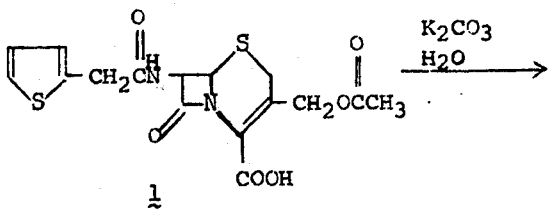

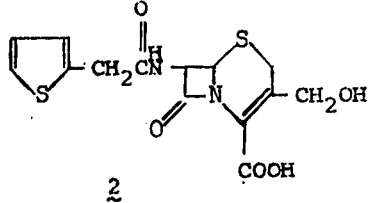

This substance was prepared according to German Offenlegungsschrift No. 2,103,014 as follows. A suspension of 8.0 g of cephalothin (1), available semi-synthetically, in 120 ml. of $H_2O$ treated with 8.6 g of $K_2CO_3$ and the resulting solution was stirred at 36° for 4.25 hours, then at 30° for 18 hours. The resulting mixture was layered with 500 ml of ethyl acetate and a solution of 10.0 ml of conc. HCl in 50 ml of $H_2O$ was added. The ethyl acetate was dried ($MgSO_4$) and removed in vacuo in yield 3.84 g (54%) of 3-hydroxymethyl-7-(2-thienylacetamido)-3-cephem-4-carboxylic acid, mp 138°–145°d. Crystallization from ethyl acetate yielded material, mp 149°–151°d (lit. mp 151.5°–152°d); ir (nujol mull): 3600–2400 (carboxyl -OH), 3450 (amide N-H), 1790 ($\beta$-lactam C=O), 1745 (acid C=O), 1650 (amide C=O), and 1510 ("amide II" band) $cm^{-1}$.

A2. Preparation of Benzhydryl 3-Hydroxymethyl-7-(2-thienylacetamido)-3-cephem-4-carboxylate (3).

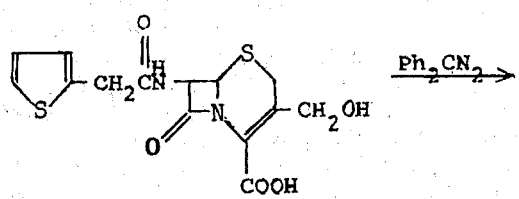

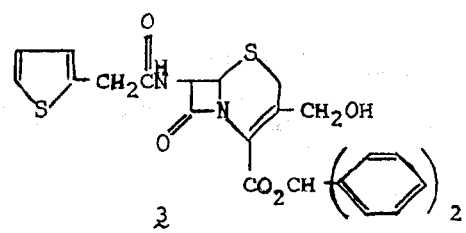

Using the procedure outlined in German patent 2,103,014, a solution of 3.84 g of the preceding acid (2) in 150 ml of tetrahydrofuran was added to 2.6 g of diazodiphenylmethane. Gas evolution started immediately. The mixture was allowed to stir at 25° for 64 hrs, then stripped in vacuo and triturated with ether to yield 6.38 g of benzhydryl 3-hydroxymethyl-7-(2-thienylacetamido)-3-cephem-4-carboxylate, mp 116°–138°d (lit mp 169°–170°d); ir (CHCl$_3$); 3500 (-OH), 1790 ($\beta$-lactam C=O), 1735 (ester C=O), 1670 (amide C=O), 1500 ("amide II" band), and 690 (monosubstituted benzene) $cm^{-1}$; nmr (dmso-d$_6$): $\delta$ 3.22 (2, s, $C_2$-C$\underline{H}_2$), 3.92 (2, s, $\alpha$-thienyl-C$\underline{H}_2$), 4.17 (1, s (broad), -OH) 4.78 (2, s, $C_3$-CH$_2$) 5.08 (1, d (J = 5 Hz), $C_6$-H), 5.77 (1, m, $C_7$-H), 6.88 (1, s, -C$\underline{H}$Ph$_2$), 6.92 (2, d (J = 3 Hz), thiophene 3- and 5-H's), 7.31 (11, s (broad), aromatic and thiophene 4-H), and 9.01 (1, d (J = 10 Hz), amide N-H).

Anal. Calcd. for $C_{27}H_{24}N_2O_5S_2$: C, 62.31; H, 4.65; N, 5.38. Found: C, 62.50; H, 4.85; N, 5.33.

A3. Preparation of Benzhydryl 3-Fluoromethyl-7-(2-thienylacetamido)-3-cephem-4-carboxylate (4).

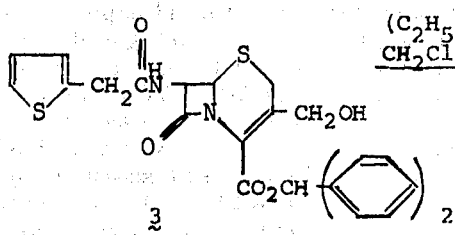

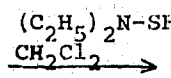 m = 0

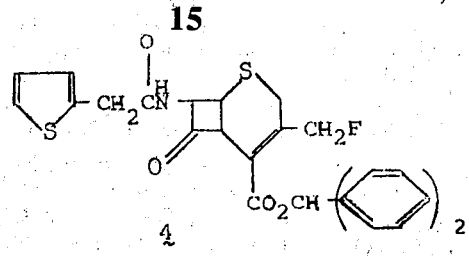

To a solution of 0.322 g (2.0 mmoles) of diethylaminosulfur trifluoride in 10 ml of CH$_2$Cl$_2$ at $-78°$C. under N$_2$ is added dropwise with stirring under anhydrous conditions a solution of 1.04 g (2.0 mmoles) of benzhydryl 3-hydroxymethyl-7-(2-thienylacetamido)-3-cephem-4-carboxylate in 10 ml of CH$_2$Cl$_2$. The mixture is stirred at $-78°$ for 0.5 hour, then poured into 50 ml of water and extracted with CH$_2$Cl$_2$. The CH$_2$Cl$_2$ layer is separated, dried (MgSO$_4$) and evaporated in vacuo. Chromatography on silica gel with CHCl$_3$ gives benzhydryl 3-fluoromethyl-7-(2-thienylacetamido-3-cephem-4-carboxylate).

EXAMPLE 2

A4.
3-Fluoromethyl-7-(2-thienylacetamido)-3-cephem-4-carboxylic acid (5)

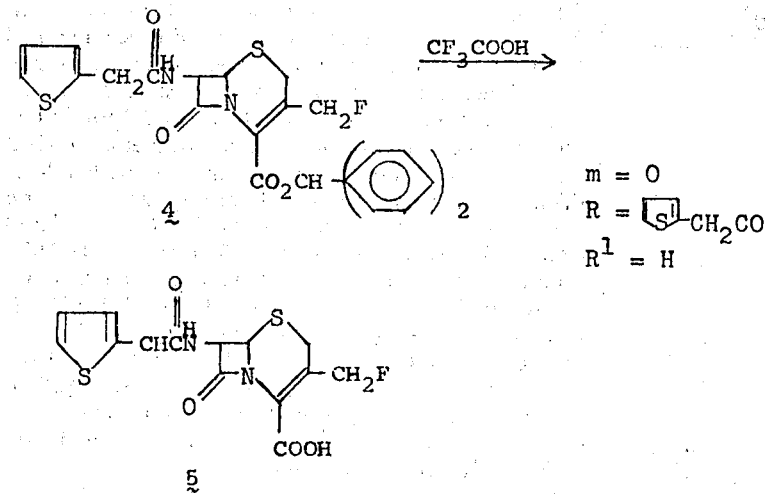

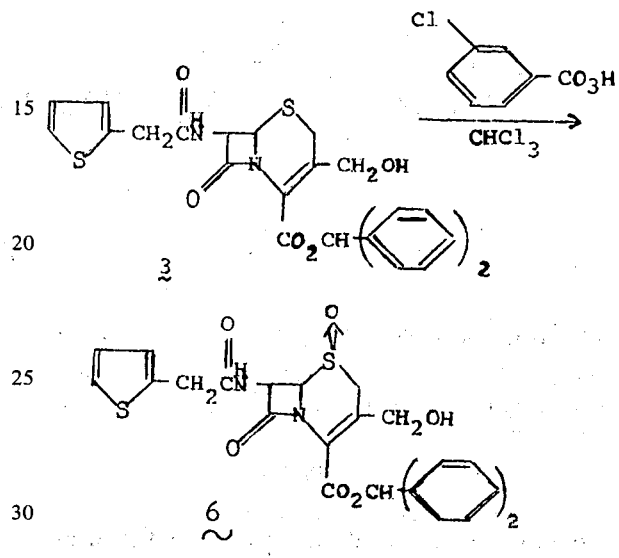

To 0.522 g (1.0 mmoles) of benzhydryl 3-fluoromethyl-3-cephem-4-carboxylate and 0.108 g anisole at 0° is added 15 ml trifluoroacetic acid and the mixture is stirred at 0° for 0.5 hrs. Then the mixture is stripped in vacuo, dissolved in ethyl acetate, washed with water, and the ethyl acetate solution dried (MgSO$_4$) and stripped in vacuo. The residue can be recrystallized from 50% ethanol to yield 3-fluoromethyl-7-(2-thienylacetamido)-3-cephem-4-carboxylic acid.

The following steps A5 through A7 represent an alternative route to compound 4.

A5. Preparation of Benzhydryl 3-Hydroxymethyl-7-(2-thienylacetamido)-3-cephem-4-carboxylate-1-oxide To a solution of 16 g of crude hydroxy ester (obtained as in A2 above) in 75 ml CHCl$_3$ at 0° was added dropwise a solution of 2.9 g of m-chloroperbenzoic acid in 50 ml of CHCl$_3$. The resulting solution was stirred 3 hrs at 0°, then washed with 5% NaHCO$_3$, dried (MgSO$_4$), and stripped in vacuo. The residue was dissolved in boiling methanol and the methanol was removed in vacuo. The resulting material was chromatographed on silica with CHCl$_3$, then 4:1 CHCl$_3$/ethyl acetate, and finally ethyl acetate, giving 4.5 g of benzhydryl 3-hydroxymethyl-7-(2-thienylacetamido)-3-cephem-4-carboxylate-1-oxide, mp 175.5°–176.5° d; ir (CHCl$_3$): 3550 (OH), 1795 ($\beta$-lactam C=O), 1720 (ester C=O), 1660 (amide C=O), 1495 ("amide II" band), and 1040 (sulfoxide) cm$^{-1}$; nmr (dmso-d$_6$): $\delta$ 3.68 (2, m, C$_2$-$\underline{H}$), 3.82 (2, s, thienyl-C$\underline{H}_2$), 4.29 (2, d (J = 5 Hz), C-3-C$\underline{H}_2$OH), 4.86 (1, d (J = 5 Hz), C$_6$ - $\underline{H}$), 5.88 (1, dd (J = 5 Hz, J′ = 8 Hz), C$_7$-H), 6.82 (1, s, -OC$\underline{H}$Ph$_2$), 6.93 (2, d (J = 3.0) Hz), thiophene 3- and 5-H), and 8.32 (11, m, phenyl and thiophene 4-$\underline{H}$).

Anal. Calcd. for C$_{27}$H$_{24}$N$_2$O$_6$S$_2$: C, 60.45; H, 4.51; N, 5.22. Found: C, 60.32; H, 4.62; N, 4.97.

A6. Preparation of Benzhydryl 3-Fluoromethyl-7-(2-thienylacetamido)-3-cephem-4-carboxylate-1-oxide (7).

N-H), 1805 (β-lactam C=O), 1725 (ester C=O), 1680 (amide C=O), 1495 ("amide II" band), and 700 (aromatic) cm$^{-1}$; mp 205.5°–207.5°d.

Anal. Calcd. for C$_{27}$H$_{23}$N$_2$O$_5$S$_2$F: C, 60.22; H, 4.28; N, 5.20; F, 3.54. Found: C, 59.40; H, 4.29; N, 5.20; F, 3.60.

A7. Benzhydryl 3-Fluoromethyl-7-(2-thienylacetamido)-3-cephem-4-carboxylate (4)

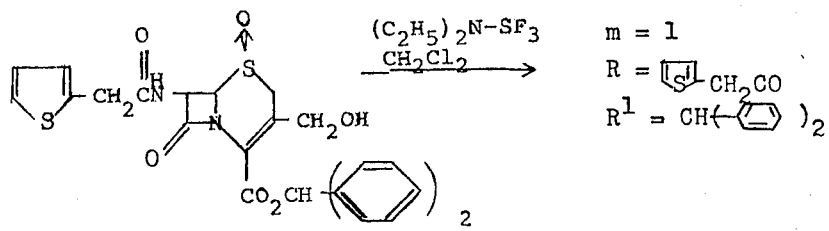

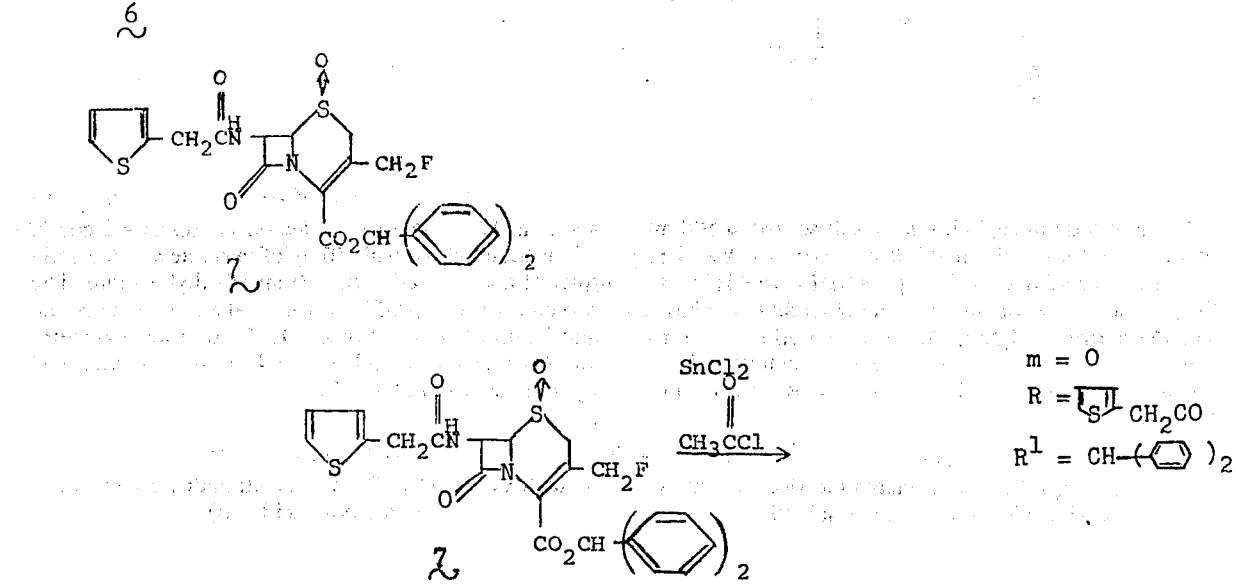

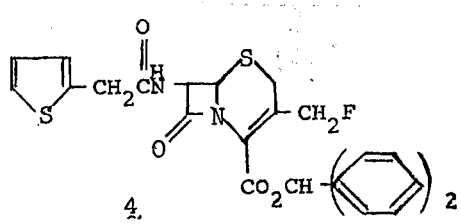

To a solution of 0.483 g (3.0 mmoles) of diethylaminosulfur trifluoride in 10 ml of CH$_2$Cl$_2$ at −78° under N$_2$ was added a solution of 1.61 g (3.0 mmoles) of benzhydryl 3-hydroxymethyl-7-(2-thienylacetamido)-3-cephem-4-carboxylate-1-oxide in 50 ml of CH$_2$Cl$_2$ and the mixture was stirred at −78° for 0.5 hrs, then poured into 100 ml of water. The CH$_2$Cl$_2$ layer was dried (MgSO$_4$) and evaporated in vacuo. The residue was chromatographed on silica gel with 9:1 CH$_2$Cl$_2$-acetone to yield 0.095 g of benzhydryl 3-fluoromethyl-7-(2-thienyl-acetamido)-3-cephem-4-carboxylate-1-oxide in fractions 12-15, rf = 0.60 on tlc with 9:1 CH$_2$Cl$_2$-acetone; ir (CHCl$_3$) 3450 (amide To a solution of 2.08 g (3.7 mmole) of benzhydryl 3-fluoromethyl-7-(2-thienylacetamido)-3-cephem-4-carboxylate-1-oxide in 15 ml CH$_3$CN and 6 ml DMF (dimethylformamide) at 0° is added 0.765 g (4.04 mmole) of anhydrous SnCl$_2$ and 1.21 g (15.4 mmole) of acetyl chloride and the resulting mixture is stirred at 0° for 1.0 hrs, then at 30° for 1.0 hour, and then poured into water and extracted with ethyl acetate. The ethyl acetate layer is washed with 3% HCl solution, 5% NaHCO$_3$ solution, and water, and then dried (MgSO$_4$) and stripped in vacuo to yield benzhydryl 3-fluoromethyl-7-(2-thienylacetamido)-3-cephem-4-carboxylate, which can be purified by the method outlined in 3 above.

EXAMPLE 3

A8.
3-Acetoxymethyl-7-(2-thienylacetamido)-3-cephem-4-carboxylic Acid (8)

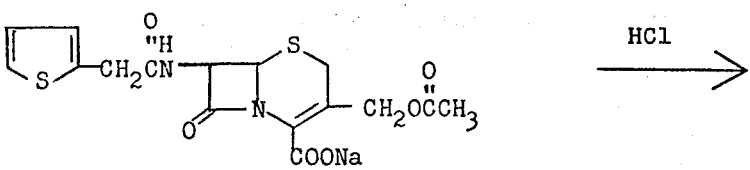
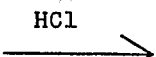

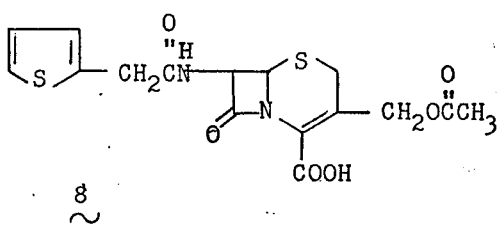

21.6 g of sodium cephalothin was dissolved in 500 ml of water and layered with 500 ml ethyl acetate. The mixture was acidified to pH 4 by addition of 6N HCl and the product was extracted into the ethyl acetate phase, which was dried (MgSO$_4$) and evaporated in vacuo to yield 20.4 g of 3-acetoxymethyl-7-(2-thienylacetamido)-3-cephem-4-carboxylic acid, mp 152°–154°.

A9.
3-Acetoxymethyl-7-(2-thienylacetamido)-2-cephem-4-carboxylic Acid Pyridine Salt (9)

Using the method outlined in German Offenlegungschrift No. 2,103,014, 20.4 g of 3-acetoxymethyl-7-(2-thienylacetamido)-3-cephem-4-carboxylic acid was dissolved in 60 ml of dry pyridine, with heating and then 6 ml of acetic anhydride was added to the cooled solution. The mixture solidified on standing for 2 hours. It was then diluted with 50 ml of pyridine and the solid filtered and washed with 150 ml of ethyl acetate. The product was recrystallized from 150 ml of ethyl acetate and 20 ml of alcohol to yield 15.4 g of 3-acetoxymethyl-7-(2-thienylacetamido)-2-cephem-4-carboxylic acid pyridine salt, mp 150°–151°d.

A10.
3-Acetoxymethyl-7-(2-thienylacetamido)-2-cephem-4-carboxylic acid (10)

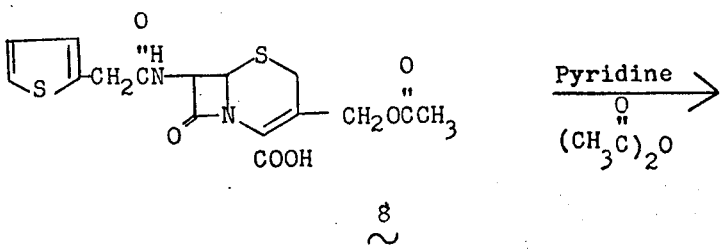
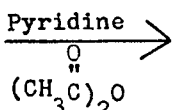

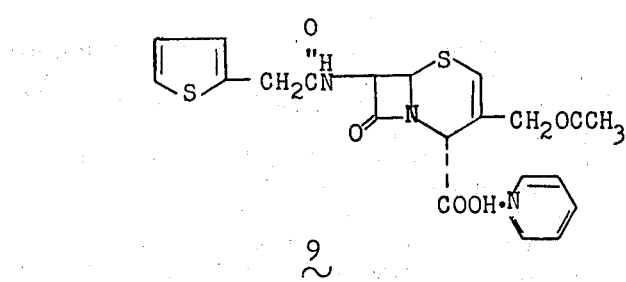

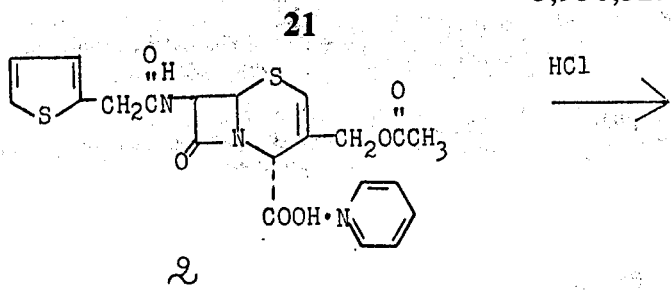

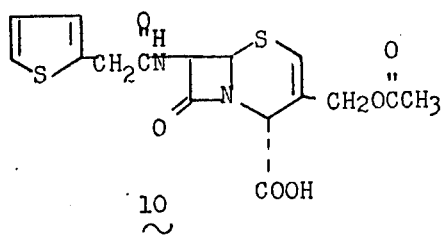

This compound was prepared according to German Offenlegungschrift 2,103,014 as follows: To 13.8 g of the pyridine salt in 500 ml of water layered with ethyl acetate was added 6N HCl until pH4 was reached. Then the acid was extracted into the ethyl acetate layer which was dried (MgSO$_4$) and evaporated to yield 11.2 g of 3-acetoxymethyl-7-(2-thienylacetamido)-2-cephem-4-carboxylic acid, mp 149°–154°.

A11.
3-Hydroxymethyl-7-(2-thienylacetamido)-2-cephem-4-carboxylic acid (11)

This compound was prepared according to German Offenlegungschrift No. 2,103,014 as follows: A suspension of 11.8 g of the acetoxymethyl compound 10 in 150 ml of water and 15 ml of acetone was treated with 21 ml of 1-N NaOH and heated to 40°. Then the mixture was kept at 50° for 17 hours, then layered with 500 ml ethyl acetate and acidified to pH4 with 2-N H$_2$SO$_4$. The product was extracted with the ethyl acetate layer, which was washed with water, dried (MgSO$_4$), and concentrated at >35° in vacuo. From this concentrate, 3.0 g of 3-hydroxymethyl >7-(2-thienylacetamido)-2-

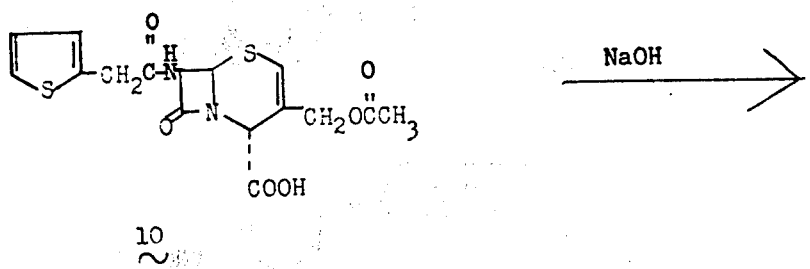

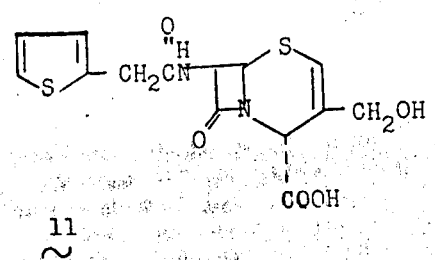

cephem-4-carboxylic acid, mp 147°–149° d, was obtained.

A12. Benzhydryl 3-Hydroxymethyl-7-(2-thienylacetamido)-2-cephem-4-carboxylate (12)

hydryl 3-hydroxymethyl-7-(2-thienylacetamido)-2-cephem-4-carboxylate, mp 168°–170°.

A13. Benzhydry 3-Fluoromethyl-7-(2-thienylacetamido)-2-cephem-4-carboxylate (13)

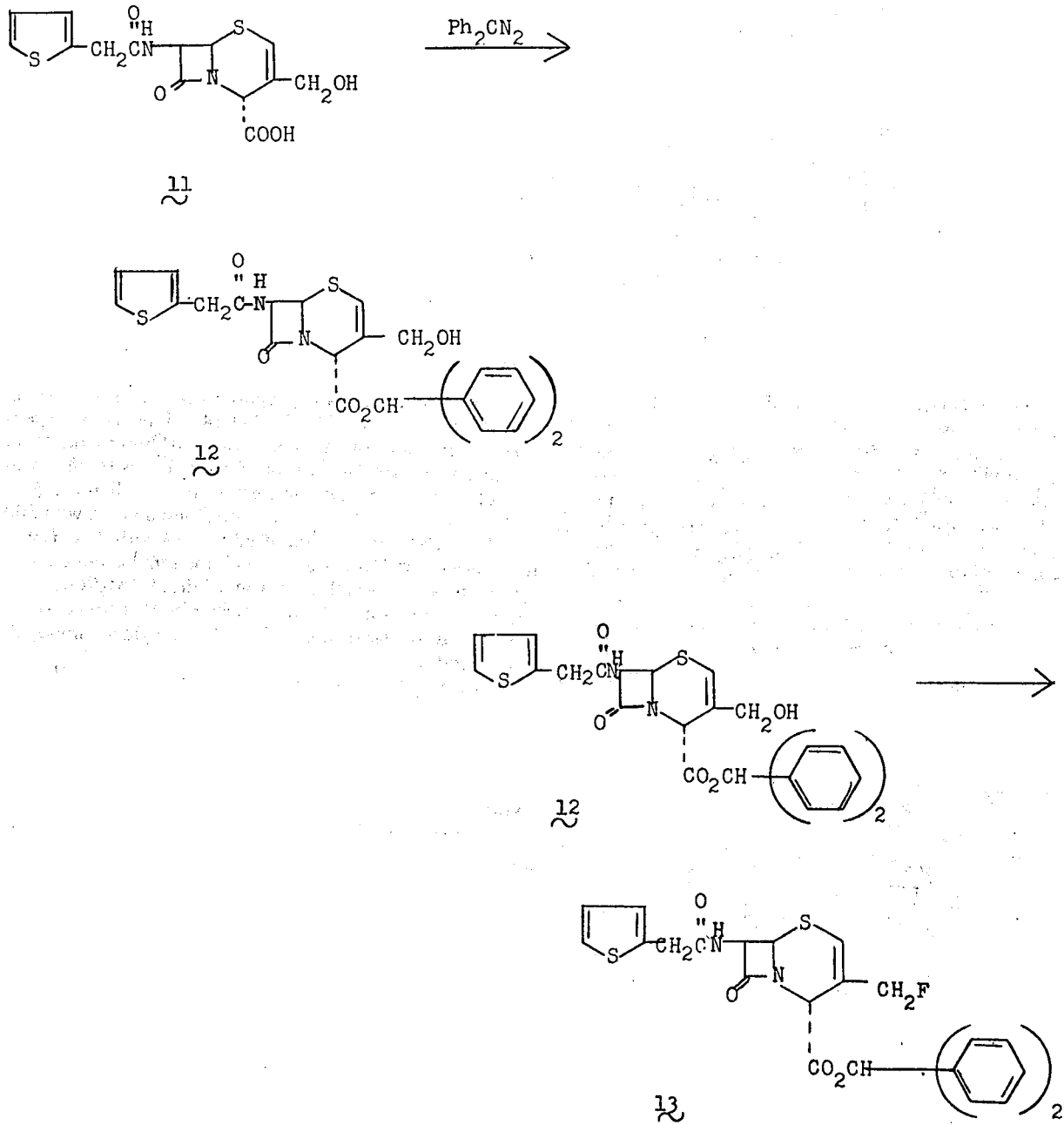

This compound was prepared according to German Offenlegungschrift 2,103,014 as follows: A solution of 3.54 g of the Δ²-hydroxymethyl acid 11 in 100 ml of tetrahydrofuran was treated with a solution of 1.94 g of diazodiphenylmethane in 50 ml of tetrahydrofuran. The mixture was stirred until the pink color had faded, and stripped of solvent in vacuo to yield 5.2 g of benz- To a solution of 0.322 g of diethylaminosulfur trifluoride in 10 ml of $CH_2Cl_2$ at $-78°$ under $N_2$ is added a solution of 1.04 g of benzhydryl-3-hydroxymethyl-7-(2-thienylacetamido)-2-cephem-4-carboxylate in 50 ml of $CH_2Cl_2$. The mixture is stirred for 0.5 hour then poured into 100 ml of $H_2O$ and the $CH_2Cl_2$ layer dried ($MgSO_4$) and evaporated in vacuo. The residue is chromatographed on silica with CHCl₃ to give benzhydryl 3-fluoromethyl-7-(2-thienylacetamido)-2-cephem-4-carboxylate, which can be purified by recrystallization from methanol.

A14. Benzhydryl 3-Hydroxymethyl-7-(2-thienylacetamido)-3-cephem-4-carboxylate-1-oxide (6)

rated in vacuo. The residue is dissolved in methanol and then concentrated to give, upon cooling, benzhydryl 3-hydroxymethyl-7-(2-thienylacetamido)-3-cephem-4-carboxylate-1-oxide.

A15. Benzhydryl 3-Fluoromethyl-7-(2-thienylacetamido)-3-cephem-4-carboxylate-1-oxide (7)

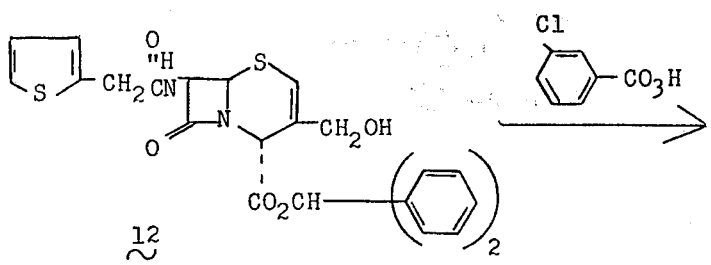

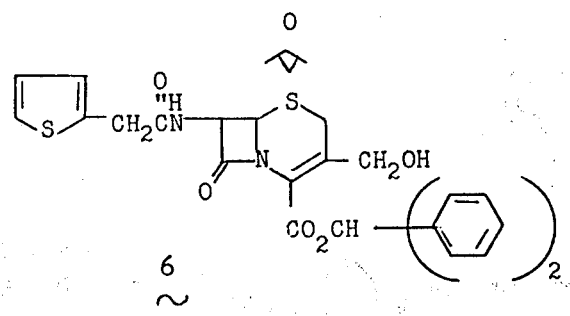

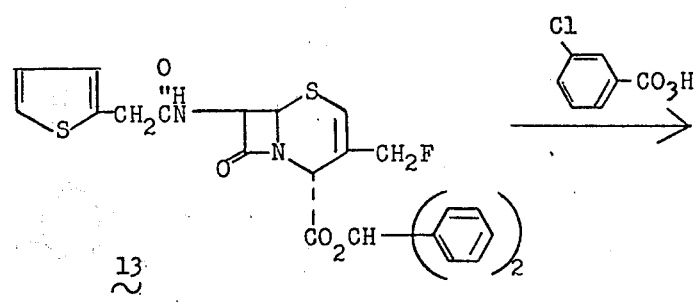

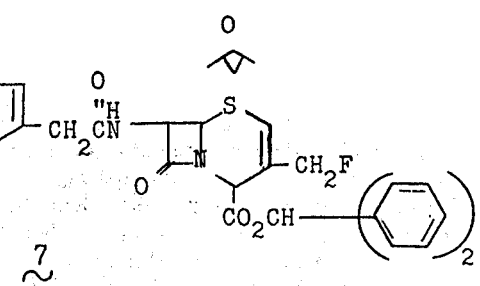

To a solution of 5.2 g of benzhydryl 3-hydroxymethyl-7-(2-thienylacetamido)-2-cephem-4-carboxylate in 50 ml of CHCl₃ at 0° is added dropwise a solution of 1.72 g of m-chloroperbenzoic acid in 25 ml of CHCl₃. The resulting solution is stirred for 3.0 hours at 0°, then washed with 5% NaHCO₃, dried (MgSO₄), and evapo- To a solution of 1.04 g of benzhydryl 3-fluoromethyl-7-(2-thienylacetamido)-2-cephem-4-carboxylate in 10 ml of CHCl₃ at 0° is added dropwise a solution of 0.35 g of m-chloroperbenzoic acid in 5 ml of CHCl₃. The solution is stirred at 0° for 2.5 hours, then diluted with CHCl₃ and washed with NaHCO₃, the dried (MgSO₄)

and evaporated in vacuo. The residue is recrystallized from methanol to yield benzhydryl 3-fluoromethyl-7-(2-thienylacetamido)-3-cephem-4-carboxylate-1-oxide.

EXAMPLE 4

A16. Benzhydryl 7-Amino-3-fluoromethyl-3-cephem-4-carboxylate p-Toluenesulfonic Acid Salt (14)

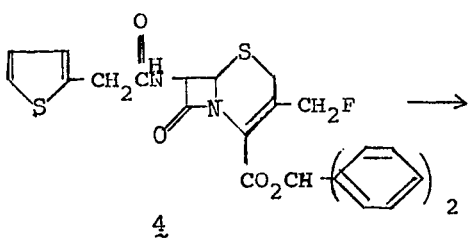

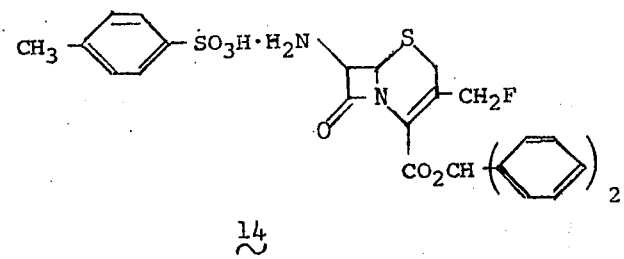

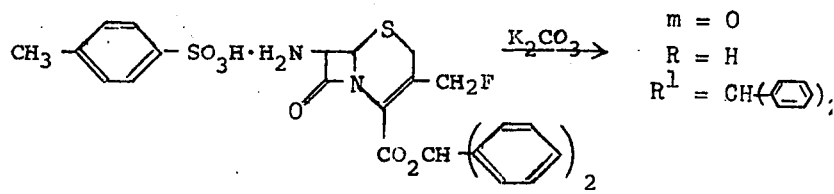

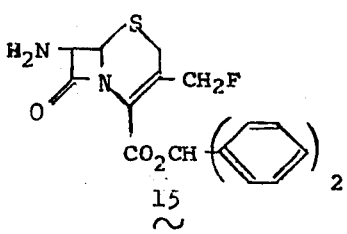

A solution of 1.20 g (2.3 mmole) of benzhydryl 3-fluoromethyl-7-(2-thienylacetamido)-3-cephem-4-carboxylate in 25 ml $CCl_4$ is cooled to below $-25°$ in a 100 ml/3-necked round bottom flask fitted with thermometer and mechanical stirrer and under $N_2$. Then 0.5 ml of N-ethyl morpholine is added and the mixture is stirred at $-25°$ while a suspension of 0.5 g of $PCl_5$ in 10 ml of dry $CCl_4$ is added over a period of 25 min. through a solid addition adapter. The resulting mixture is stirred at 0° for 30 min, then cooled to below $-25°$ again and treated with 0.5 ml of N-ethyl morpholine in 16 ml of dry methanol. This solution is stirred at 0° for 2 hrs and then poured into 30 ml of $H_2O$ in a separatory funnel and the pH was adjusted to just over 7 (just lime green to pH paper) by the addition of conc. NaOH solution. The mixture is shaken well and the $CCl_4$ layer is separated and dried (MgSO$_4$), and added to a solution of 0.40 g of p-toluenesulfonic acid hydrate in 10 ml of ethyl acetate. The resulting solution is allowed to stand in a cold room for about 5 days to give the p-toluenesulfonic acid salt of benzhydryl 7-amino-3-fluoromethyl-3-cephem-4-carboxylate.

EXAMPLE 5

A17. Benzhydryl 7-Amino-3-fluoromethyl-3-cephem-4-carboxylate (15)

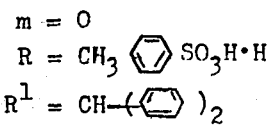

To a suspension of 1.11 g of the p-toluenesulfonic acid salt of benzhydryl 7-amino-3-fluoromethyl-3-cephem-4-carboxylate in 50 ml of ether, 50 ml of water is added. The pH can be adjusted to 7 by the addition of 5% aq. $K_2CO_3$ solution, and the ether layer separated and filtered to remove insoluble material, and dried over MgSO$_4$. Removal of the ether in vacuo gives the amino ester 15 (benzhydryl 7-amino-3-fluoromethyl-3-cephem-4-carboxylate) as a thick oil which can be used in procedure A18. below.

EXAMPLE 6

A18. Benzhydryl 3-Fluoromethyl-7-(3-[1,2,5-thiadiazolyl]acetamido)-3-cephem-4-carboxylate (16)

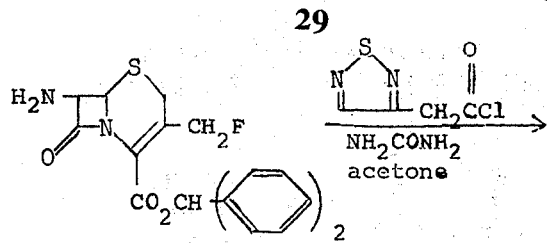
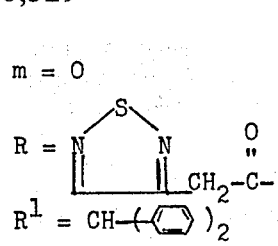

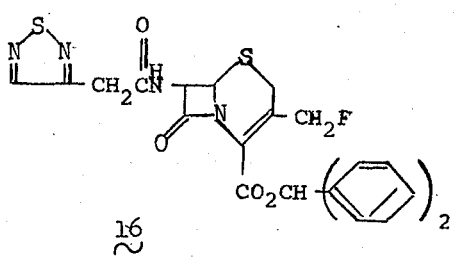

The residue from procedure A17. can be dissolved in 15 ml acetone and about 0.35 g of urea added. When a solution of 0.45 g of 3-(1,2,4-thiadiazole)acetyl chloride in 10 ml acetone is added and the mixture stirred at 25° for 1.0 hour, then filtered and stripped in vacuo, chromatography of the residue on silica with $CHCl_3$ yields benzhydryl 3-fluoromethyl-7-(3-[1,2,4-thiadiazolyl]acetamido-3-cephem-4-carboxylate.

EXAMPLE 7

A19. 3-Fluoromethyl-7-(3-[1,2,5-thiadiazolyl]-acetamido)-3-cephem-4-carboxylic acid (17)

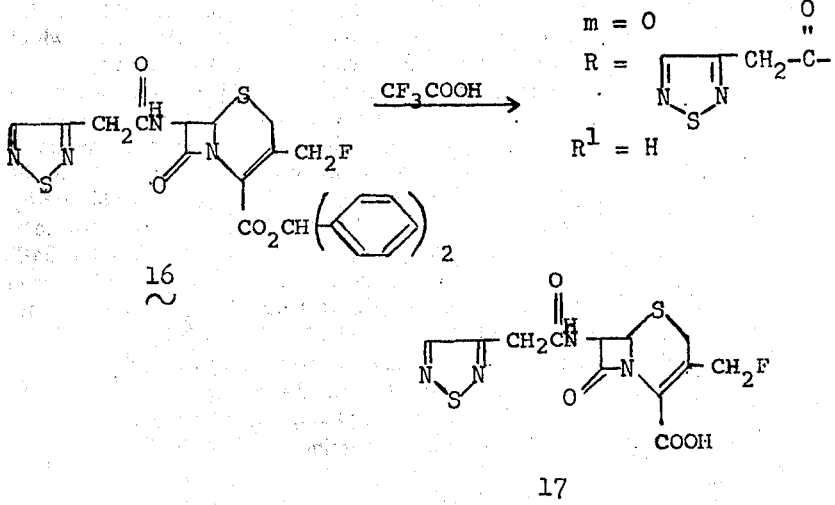

EXAMPLE 8

A20. Preparation of 2,2,2-Trichloroethyl 6-Phenylacetamidopenicillanate (19)

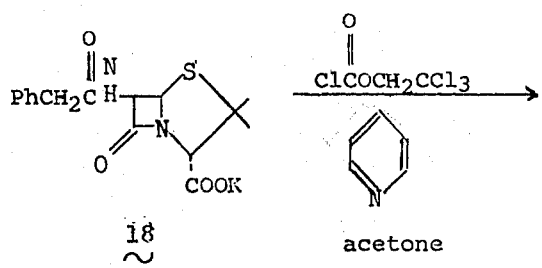

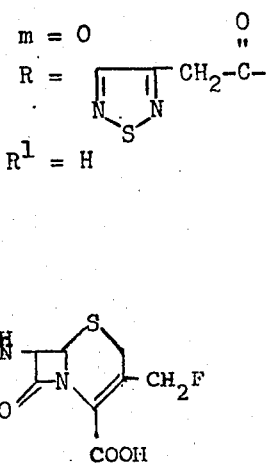

To 0.524 g (1.0 mmoles) of benzhydryl 3-fluoromethyl-7-(3-(1,2,5-thiadiazolyl)acetamido)-3-cephem-4-carboxylate and 0.108 g anisole at 0° is added 15 ml trifluoroacetic acid and the mixture is stirred at 0° for 0.5 hours. Then the mixture is stripped in vacuo, dissolved in ethyl acetate, washed with water, and the ethyl acetate solution is dried ($MgSO_4$) and stripped in vacuo. The residue can be recrystallized from 50% alcohol to yield 3-fluoromethyl-7-(3-[1,2,5-thiadiazolyl]-acetamido)-3-cephem-4-carboxylic acid.

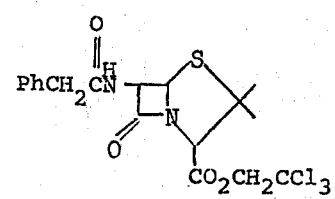

In the manner described in J. Org. Chem., 36, 1264 (1971), a mixture of 85 g of penicillin G potassium salt, 1000 ml of dry acetone, and 27 g of pyridine cooled to 0° in an ice bath was added to a solution of 48 g of 2,2,2-trichloroethyl chloroformate in 300 ml of acetone and the mixture was stirred at 0° for 18 hrs. The mixture was then filtered and the filtrate was heated to 40°, and the warm filtrate was diluted with water until cloudy. The resulting solution was put in the cold room overnight, then filtered to yield 80 g after drying overnight in a vacuum desiccator. The filtrate was diluted with an equal volume of water and chilled overnight. This yielded 15 g, for a total of 95 g (95%) of 2,2,2-trichloroethyl 6-phenylacetamidopenicillanate, mp 159°–161° (lit mp 160°–161°); ir (CHCl$_3$): 3400 (amide N-H), 1790-1770 (broad, β-lactam and ester C=O's), 1680 (amide C=O) and 1500 ("amide II") cm$^{-1}$; nmr (CDCl$_3$): δ1.52 (6H, s, C(C$\underline{H}_3$)$_2$), 3.63 (2H, s, benzyl-C$\underline{H}_2$), 4.52 (1H, s, 4-$\underline{H}$), 4.78 (2H, s, -C$\underline{H}_2$CCl$_3$), 5.67 (2H, m, 6- and 7-$\underline{H}$), 6.40 (1H, d(J=8), N$\underline{H}$), and 7.34 (5H, s, aromatic).

A21. Preparation of 2,2,2-Trichloroethyl 6-Phenylacetamidopenicillanate-1-oxide (20)

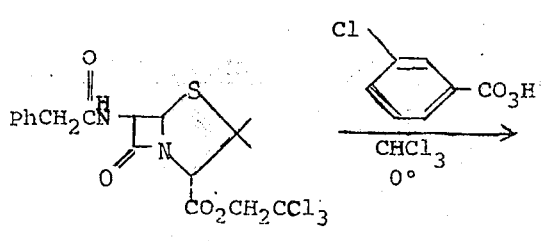

19

20

Following the procedure described in J. Org. Chem., 36, 1264 (1971), to 25 g of 2,2,2-trichloroethyl 6-phenylacetamidopenicillanate in 265 ml of chloroform cooled to 0° was added dropwise a solution of 11.66 g of m-chloroperbenzoic acid in 130 ml of chloroform. The resulting solution was stirred at 0° for 2 hrs., then washed with 5% NaHCO$_3$ solution, dried over anhydrous MgSO$_4$, filtered, and evaporated to dryness on a rotary evaporator. The resulting residue was triturated with ether and filtered. Isolated was a total of 25.2 g (99%) of 2,2,2-trichloroethyl 6-phenylacetamidopenicillanate-1-oxide, mp 167°–169° (lit mp 167°–169°); ir (CHCl$_3$): 3400 (amide N-H), 1805 (β-lactam C=O), 1770 (ester C=O), 1695 (amide C=O), 1500 ("amide II" band), and 1040 (sulfoxide) cm$^{-1}$; nmr (CDCl$_3$): δ 1.27 (s, 3 H, β-2-C$\underline{H}_3$), 1.73 (s, 3H, α-2-C$\underline{H}_3$), 3.57 (2H, s, benzyl -C$\underline{H}_2$), 4.73 (2H, m, -C$\underline{H}_2$CCl$_3$), 4.98 (1H, d (J = 5Hz), 6-$\underline{H}$), 5.89 (1H, doublet of doublets (J = 5Hz, J' = 10 Hz), 7-$\underline{H}$), 6.90 (1H, d (J = 10 Hz), amide N-$\underline{H}$), and 7.26 (5H, singlet, aromatic).

A22. Preparation of 2,2,2-Trichloroethyl 7-Phenylacetamido-3-methyl-3-cephem-4-carboxylate (21)

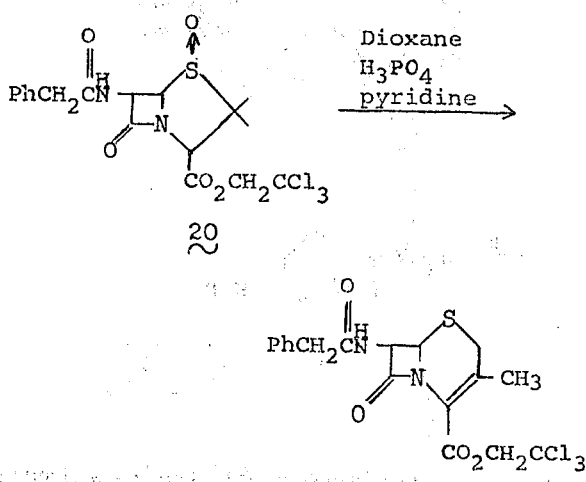

A solution of 9.64 g of 2,2,2-trichloroethyl 6-phenylacetamido-penicillanate-1-oxide, 0.45 g of 87% phosphoric acid, and 0.32 g of pyridine in 200 ml of dry dioxane was heated under reflux for 16 hrs. The flask was under a Soxhlet apparatus and condenser containing 15 g of molecular sieves in the extraction thimble to dry the distillate before it was returned to the reaction flask. After the heating period was completed, the solvent was evaporated on a rotary evaporator using a vacuum pump. The residue was dissolved in 200 ml of methylene chloride and washed with 100 ml each of water, 2N HCl solution, water, 3% NaHCO$_3$ solution, and water (saturated NaCl solution was added to the aqueous phase to break up any emulsions which formed during these extractions). The resulting methylene chloride solution was dried over anhydrous MgSO$_4$, filtered, and evaporated on a rotary evaporator. The residue was triturated with 25 ml of methanol. After crystallization was complete, the solid was filtered, yielding 3.8 g (41%) of 2,2,2-trichloroethyl 7-phenylacetamido-3-methyl-3-cephem-4-carboxylate, mp 160°–161° (lit mp 162°–164°); ir (CHCl$_3$): 3400 (amide N-H), 1785 (β-lactam C=O), 1745 (ester C=O), 1695 (amide C=O) and 1500 ("amide II" band) cm$^{-1}$; nmr (CDCl$_3$): δ2.17 (3H, s, 3-C$\underline{H}_3$), 3.35 (2H, m, 2-C$\underline{H}_2$), 3.64 (2H, s, benzyl C$\underline{H}_2$), 4.88 (2H, m, -C$\underline{H}_2$CCl$_3$), 6.65 (1H, d (J = 4.5 Hz), 6-H), 5.83 (1H, doublet of doublets (J = 4.5 Hz, J = 9 Hz), 7-$\underline{H}$), 6.42 (1H, d (J = 9 Hz), amine N-H), and 7.30 (5H, s, aromatic).

A23. Preparation of 2,2,2-Trichloroethyl 7-Phenylacetamido-3-methyl-3-cephem-4-carboxylate-1-oxide (22)

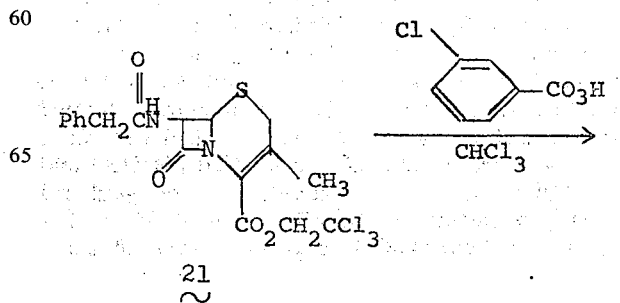

21

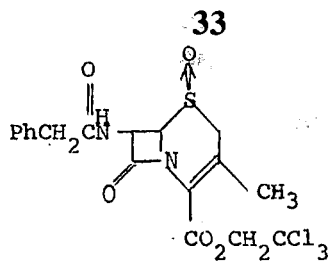

To a solution of 2.32 g of ester 21 in 25 ml CHCl₃ at 0° was added a solution of 1.1 g of m-chloroperbenzoic acid in 15 ml of CHCl₃ and the mixture was stirred at 0° for 2.0 hrs. The mixture was then washed with 5% NaHCO₃, dried (MgSO₄) and stripped in vacuo. Trituration of the residue with ether followed by filtration yielded 2.6 g of 2,2,2-trichloroethyl 7-phenylacetamido-3-methyl-3-cephem-4-carboxylate-1-oxide, mp 194°–195.5° d; ir (CHCl₃): 3500 (amide N-H), 1810 (β-lactam C=O), 1760 (ester C=O), 1700 (amide C=O), 1500 ("amide II" band), and 1040 (sulfoxide) cm⁻¹.

Anal. Calcd. for $C_{18}H_{17}Cl_3N_2O_5S$: C, 45.00; H, 3.55; N, 5.83. Found: C, 44.92; H, 3.43; N, 5.52.

A24. preparation of 2,2,2-Trichloroethyl 3-Bromomethyl-7-phenylacetamido-3-cephem-4-carboxylate-1-oxide (23)

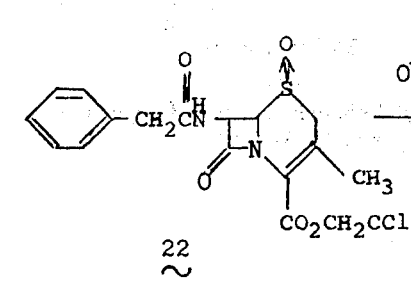

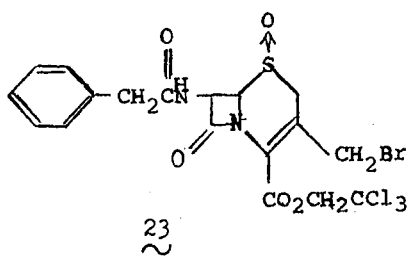

In the manner described in German Patent 2,042,169, a degassed solution of 5.0 g (0.010 mmoles) of sulfoxide 22 and 2.8 g of N-bromosuccinimide in 400 ml of ethylenedichloride at 0° under N₂ was irradiated at 0° for 1.0 hour with a 100 w. medium presssure Hanovia mercury lamp. The mixture was then washed with 2-100 ml portions of water and the combined aqueous layers were washed with 50 ml of ethylene dichloride. The combined ethylene dichloride solutions were dried (MgSO₄), stripped in vacuo, and the residue was chromatographed on silica gel with 9:1 CH₂Cl₂-acetone, yielding 2.53 g (43%) of 2,2,2-trichloroethyl 3-bromomethyl-7-phenylacetamido-3-cephem-4-carboxylate-1-oxide, mp 160°–163°d (lit mp 162°–164° d); nmr (dmso-d₆): δ3.40 and 3.87 (AB, 2 ($J_{AB}$ =14 Hz), C₂-H's), 3.36 and 4.04 (AB, 2, $J_{AB}$ = 19 Hz), thienyl (α-CH₂), 4.39 and 4.76 (AB, 2 ($J_{AB}$ = 11 Hz), -C₃-CH₂-Br), 5.00 (d, 1 (J = 5), C₆-H), 4.93 and 5.35 (AB, 2 ($J_{AB}$ = 13), -CH₂CCl₃), 5.90 (dd, 1 (J = 5Hz, J' = 8 Hz), C -H), 7.25 (s, 5, phenyl-H), and 8.25 (d, 2 (J = 8Hz) amide N-H).

A25. 2,2,2-Trichloroethyl 3-Hydroxymethyl-7-phenylacetamido-3-cephem-4-carboxylate-1-oxide (24)

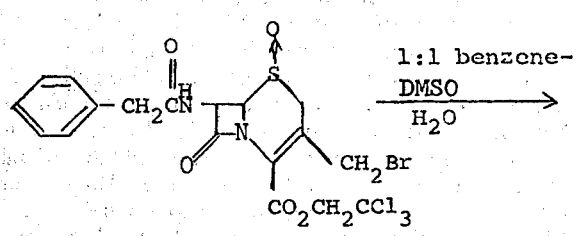

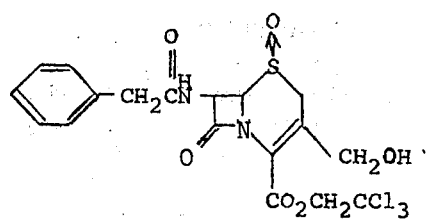

To a solution of 0.461 (0.82 mmole) of 2,2,2-trichloroethyl 3-bromoethyl-7-phenylacetamido-3-cephem-4-carboxylate-1-oxide in 20 ml of 1:1 benzene-dimethylsulfoxide (DMSO) is added 0.150 ml (8.2 mmoles) of water and the mixture is stirred at 25° for 7 days. Then the mixture is poured into 100 ml of H₂O and extracted with ethyl acetate. The ethyl acetate is dried (MgSO₄) and evaporated in vacuo to yield 2,2,2-trichloroethyl 3-hydroxymethyl-7-phenylacetamido-3-cephem-4-carboxylate-1-oxide, which can be purified by recrystallization from methanol.

A26. 2,2,2-Trichloroethyl 3-Fluoromethyl-7-phenylacetamido-3-cephem-4-carboxylate-1-oxide (25).

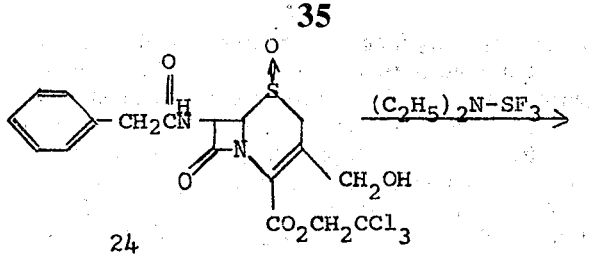

24

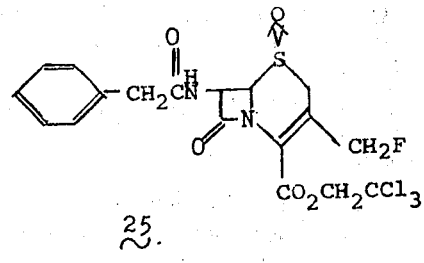

25 m = 1
R = ⟨phenyl⟩-CH$_2$CO
R$^1$ = CH$_2$CCl$_3$

To a solution of 0.242 g (1.5 mmoles) of diethylaminosulfurtrifluoride in 15 ml of CH$_2$Cl$_2$ at $-78°$ under N is added dropwise with stirring a solution of 0.740 g (1.5 mmoles) of 2,2,2-trichloromethyl 3-hydroxymethyl-7-phenylacetamido-3-cephem-4-carboxylate-1-oxide in 25 ml of CH$_2$Cl$_2$. The mixture is stirred at $-78°$ for a few hrs, then is poured into 100 ml of water and extracted with CH$_2$Cl$_2$. The CH$_2$Cl$_2$ layer is separated, dried (MgSO$_4$), and evaporated in vacuo. Chromatography on silica gel with 9:1 CH$_2$Cl$_2$-acetone purifies 2,2,2-trichloroethyl 3-fluoromethyl-7-phenylacetamido-3-cephem-4-carboxylate-1-oxide.

To a solution of 0.494 g (1.0 mmole) of 2,2,2-trichloroethyl 3-fluoromethyl-7-phenylacetamido-3-cephem-4-carboxylate-1-oxide in 5 ml CH$_3$CN and 2 ml DMF at 0° is added 0.207 g (1.1 mmole) anhydrous SnCl$_2$ and 0.40 g (5 mmole) acetyl chloride and the resulting mixture is stirred at 0° for 1.0 hrs, then at 25° for 1.0 hour, and then poured into water and extracted with ethyl acetate. The ethyl acetate layer is washed with 3% HCl solution, 5% NaHCO$_3$ solution, and water, and then dried (MgSO$_4$) and stripped in vacuo to give 2,2,2-trichloroethyl 3-fluoromethyl-7-phenylacetamido-3-cephem-4-carboxylate, which can be purified by chromatography on silica gel with chloroform.

EXAMPLE 9
A27. 2,2,2-Trichloroethyl 3-Fluoromethyl-7-phenylacetamido-3cephem-4-carboxylate (26)

EXAMPLE 10
A28. 3-Fluoromethyl-7-phenylacetamido-3-cephem-4-carboxylic Acid (27).

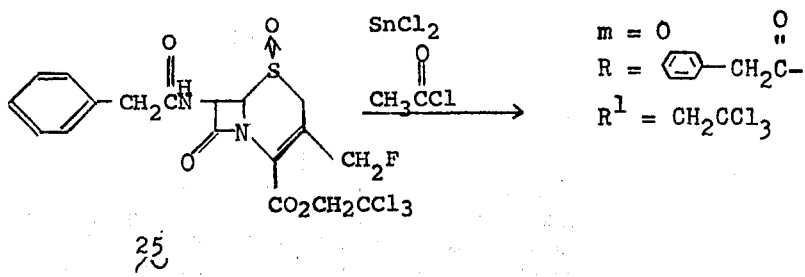

25 m = 0
R = ⟨phenyl⟩-CH$_2$C-
        ||
        O
R$^1$ = CH$_2$CCl$_3$

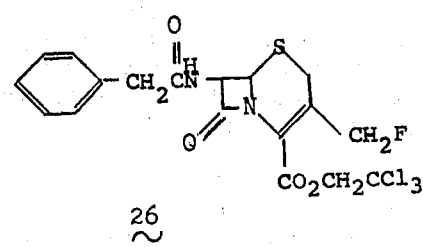

26

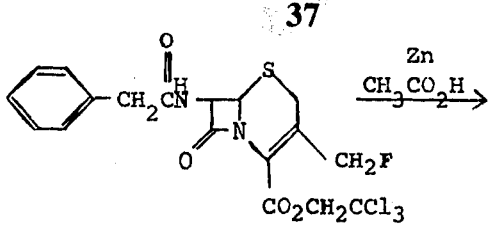 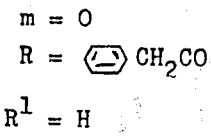

26

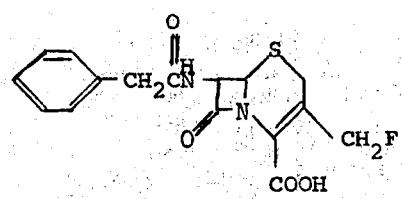

27

To 0.239 g (0.5 mmoles) of 2,2,2-trichloromethyl 3-fluoromethyl-7-phenylacetamido-3-cephem-4-carboxylate in 5 ml of glacial acetic acid at 0° is added 0.325 g (5 mmole) of zinc dust and the mixture is stirred at 0° for 3.0 hours. When the mixture is poured into 25 ml water, extracted with ethyl acetate, and the ethyl acetate solution was dried (MgSO$_4$) and stripped in vacuo, the residue can be recrystallized from 50% alcohol to give 3-fluoromethyl-7-phenylacetamido-3-cephem-4-carboxylic acid.

EXAMPLE 11

B1. Preparation of Benzhydryl 3-Formyl-7-(2-thienylacetamido)-3-cepham-4-carboxylate (28).

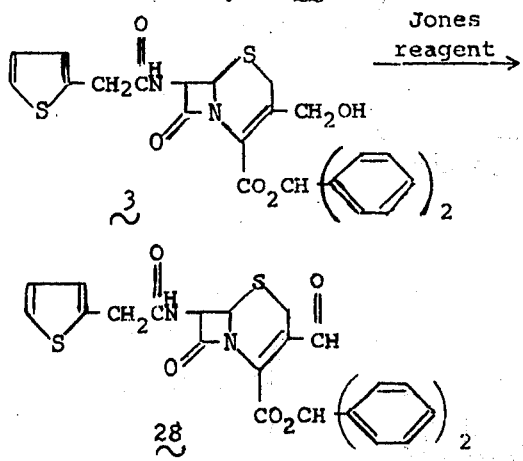

As described in German Pat. No. 2,103,014, a solution of 3.3 g of benzhydryl 3-hydroxymethyl-7-(2-thienylacetamido)-3-cepham-4-carboxylate (3) in 150 ml acetone was cooled to 0° and 1.90 ml of 8N CrO$_3$ in H$_2$SO$_4$ (Jones reagent) was added in 0.10 ml increments over the period of 5.0 min. The resulting mixture was stirred for 40 min. at 0°, then an additional 0.30 ml of oxidant was added. The mixture was stirred an additional 10 min., then poured into 450 ml satd. NaCl layered with 300 ml ethyl acetate. The organic layer was washed with water, dried (MgSO$_4$), and stripped in vacuo. The resulting residue was chromatographed on silica with benzene, then 4:1 benzene ethyl acetate to yield 0.564 g of benzhydryl 3-formyl-7-(2-thienylacetamido)-3-cepham-4-carboxylate; ir (CHCl$_3$): 3400 (amide N-H), 2720 (aldehyde H), 1810 ($\beta$-lactam C=O), and 1507 ("amide II" band) cm$^{-1}$; uv max C$_2$H$_5$OH): 298 nm (7750), 335 nm (7250), and 450 nm (620); nmr (CDCl$_3$): $\delta$ 3.17 and 3.90 (AB, 2 (J$^{AB}$=19 Hz), C$_2$-CH$_2$), 3.95 (s, 2, $\alpha$-thienyl CH$_2$), 4.91 (d, 1 (J = 5 Hz), C$_6$-H), 5.92 (dd, 1 (J = 5 Hz), J' = 10 Hz), C$_7$-H, 7.03 (s, 1, -CO$_2$CHPh$_2$), 7.31 (m, 13, phenyl & thiophene -H), 6.78 (d, 1 (J = 10 Hz), amide N-H), and 9.60 (s, 1, aldehyde -H).

B2. Preparation of Benzhydryl 3-Difluoromethyl-7-(2-thienylacetamido)-3-cephem-4-carboxylate (29)

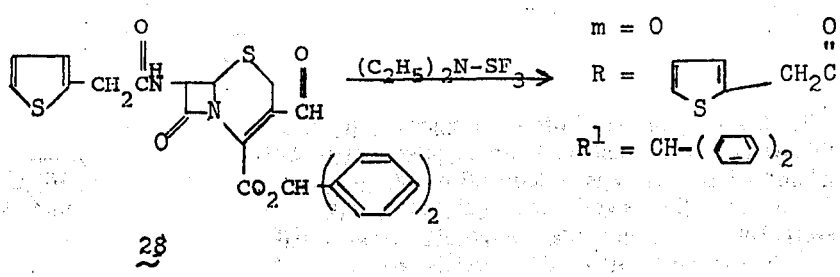

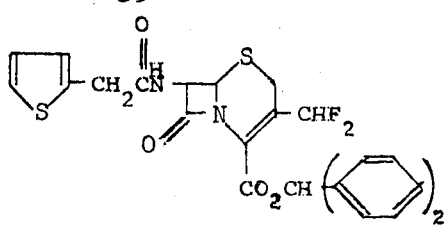

29

A solution of 0.518 g of benzhydryl 3-formyl-7-(2-thienylacetamido)-3-cephem-4-carboxylate and 1.0 ml of diethylaminosulfur trifluoride in 25 ml CH$_2$Cl$_2$ was stirred at 27° for 2.0 hrs and then poured into 25 ml of water. The CH$_2$Cl$_2$ phase was dried (MgSO$_4$) and stripped in vacuo. The residue was chromatographed on silica with CHCl$_3$ to yield 0.264 g (49%) of a 1:1 mixture of $\Delta^3$:$\Delta^2$ benzhydryl 3-difluoromethyl-7-(2-thienylacetamide)-cephem-4-carboxylates; ir (CHCl$_3$) 3450 (amide N-H), 1820 (β-lactam C=O), 1750 (ester C=O), 1695 (amide C=O), and 1510 ("amide II" band) cm$^{-1}$; $^{19}$F nmr (CHCl$_3$) δ 116.43 (d (J$_{HF}$ = 57 Hz), -CHF$_2$ (one of $\Delta^2$+$\Delta^3$ isomers)) and 115.82 (d(J$_{HF}$=57 Hz), -CHF$_2$ (other isomer)); $^1$H nmr (CDCl$_3$) δ 3.5 (2, m, C$_2$-CH$_2$ ($\Delta^3$-isomer)), 3.74 (2, s, thienyl -CH$_2$), 4.94 (1, d(J = 6 Hz), C$_6$-H), 5.91 (1, dd (J = 6Hz, J' = 10 Hz), C$_7$ -H), 6.72 (1, t (J$_{HF}$ = 57 Hz), -CHF$_2$), and 7.3 (13, m, aryl + thiophene -H); uv max (C$_2$H$_5$OH) 265 nm (7400).

Anal. Calcd. for C$_{27}$H$_{22}$N$_2$O$_4$S$_2$F$_2$: C, 59.99; H, 4.10; N, 5.18. Found: C, 59.82; H, 3.94; N, 5.01.

EXAMPLE 12

B3. 3-Difluoromethyl-7-(2-thienylacetamido)-3-cephem-4-carboxylic Acid (30)

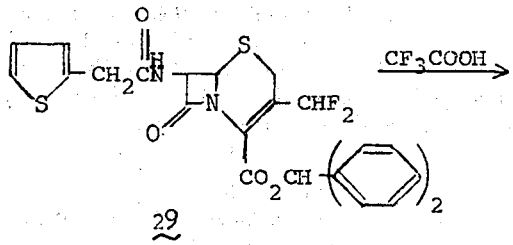 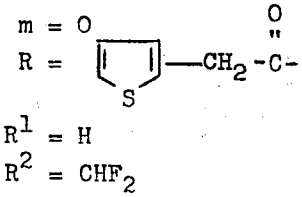

29

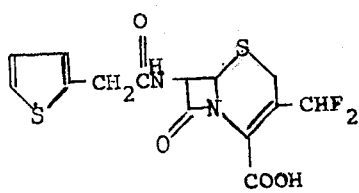

30

To 0.190 g of benzhydryl 3-difluoromethyl-7-(2-thienylacetamido)-cephem-4-carboxylate (a mixture of $\Delta^2$ and $\Delta^3$ isomers) was added 0.25 ml of anisole and 1.0 ml of trifluoroacetic acid and the mixture was swirled at 27° for 5 min., then evaporated in vacuo. The residue was taken up in ethyl acetate and extracted with 5% NaHCO$_3$ solution. The NaHCO$_3$ solution was washed once with ethyl acetate, then brought to pH3 by the addition of dilute HCl and extracted with ethyl acetate. This ethyl acetate solution was dried (MgSO$_4$) and evaporated in vacuo to yield 0.103 g (79%) of a 3:1 mixture of $\Delta^2$:$\Delta^3$ 3-difluoromethyl-7-(2-thienylacetamido)cephem-4-carboxylic acids, which was purified for analysis by crystallization from ethyl acetate-pentane; ir (KBr pellet) 3650-2500 (caroxyl -OH), 1770 (β-lactam C=O), 1725 (carboxyl C=O), 1675 (amide C=O), and 1525 ("amide II" band) cm$^{-1}$; uv max (C$_2$H$_5$OH) 235 nm (10,500) and 265 nm (4900).

Anal. Calcd. for C$_{14}$H$_{12}$N$_2$O$_4$S$_2$F$_2$: C, 44.92; H, 3.23; N, 7.48. Found: C, 44.61; H, 3.51; N, 7.23.

B4. Preparation of Benzyhydryl 3-formyl-7-(2-thienylacetamido)-3-cephem-4-carboxylate-1-oxide (31).

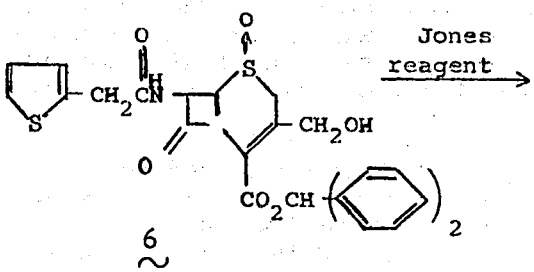

6

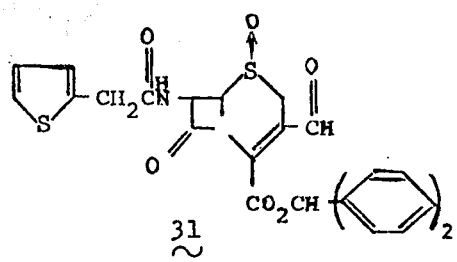

31

As described in Belgian Patent 770,531, to a solution of 1.80 g (3.4 mmole) of benzhydryl 3-hydroxymethyl-7-(2-thienylacetamido)-3-cephem-4-carboxylate-1-oxide in 100 ml of acetone at 0° was added over the period of 2 min. 0.90 ml of 8N CrO₃ in H₂SO₄ and the mixture was stirred at 0° for 5 min., then poured into a mixture of 300 ml ethyl acetate and 300 ml of water and the ethyl acetate layer was washed with water, dried (MgSO₄) and evaporated in vacuo. The residue was chromatographed on silica with CHCl₃ to yield 0.716 g of benzhydryl 3-formyl-7-(2-thienylacetamido)-3-cephem-4-carboxylate-1-oxide after crystallization from methanol; uv max (C₂H₅OH): 269 nm (4600), 292 nm (4300), and 355 nm (1760); nmr (dmso-d₆): 3.75 and 4.32 (AB, 2 ($J_{AB}$ = 19 Hz), C$_2$-CH$_2$), 3.88 (s, 2, α-thienyl CH$_2$), 5.08 (d, 1 (J = 5 Hz), C$_6$-H), 6.18 (dd, 1 (J = 5 Hz, J' = 8.5 Hz), C -H), 7.17 (1, s, -CO$_2$CH Ph$_2$), 7.02 (d, 2 (J = 3.0 Hz), thiophene 3- and 5-H), 7.44 (10, s, phenyl-H), 8.72 (d, 1 (J = 8.5 Hz), amide N-H), and 9.85 (s, 1, aldehyde-H).

B5. Benzhydryl 3-Difluoromethyl-7-(2-thienylacetamido)-3-cephem-4-carboxylate-1-oxide (32)

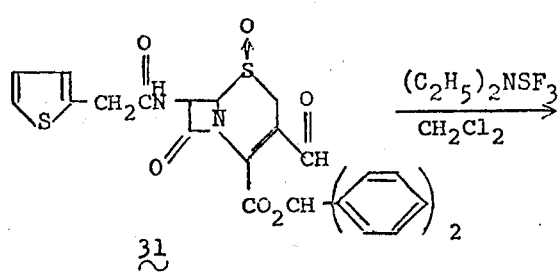

To a solution of 0.322 g of diethylaminosulfur trifluoride in 20 ml of CH₂Cl₂ at 25° under N₂ is added a solution of 1.12 g (2.1 mmoles) of benzhydryl 3-formyl-7-(2-thienylacetamido)-3-cephem-4-carboxylate-1-oxide in 20 ml of CH₂Cl₂. The mixture is stirred at 25° for 1.0 hour, then poured into 100 ml of water and extracted with CH₂Cl₂. The CH₂Cl₂ layer can be separated, dried (MgSO₄), and evaporated in vacuo. Chromatography on silica gel with 1:1 cyclohexane/ethyl acetate gives benzhydryl 3-difluoromethyl-7-(2-thienylacetamido)-3-cephem-4-carboxylate-1-oxide.

EXAMPLE 13

B6. Benzhydryl 3-Difluoromethyl-7-(2-thienylacetamido)-3-cephem-4-carboxylate (29).

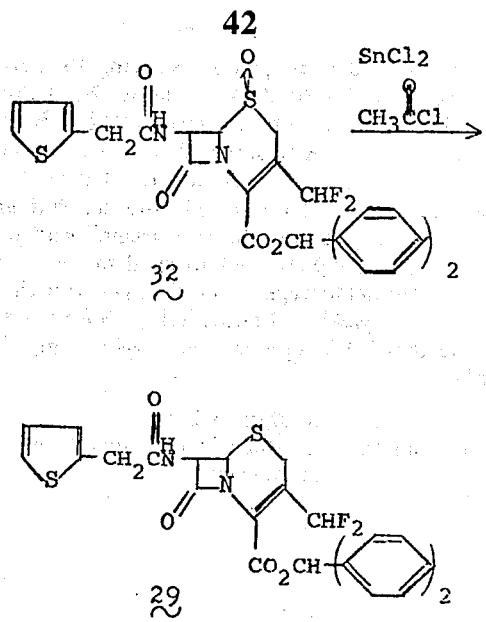

The compound 29 can also be made as follows:

To a solution of 1.22 g (2.2 mmole) of benzhydryl 3-difluoromethyl-7-(2-thienylacetamido)-3-cephem-4-carboxylate-1-oxide (25) in 10 ml CH₃CN and 3 ml DMF at 0° is added 0.455 g (2.4 mmole) anhydrous SnCl₂ and 0.70 g (9.0 mmole) acetyl chloride and the resulting mixture stirred at 0° for 1.0 hr., then at 25° for 1.0 hr., and then poured into water and extracted with ethyl acetate. The ethyl acetate layer when washed with 3% HCl solution, 5% NaHCO₃ solution, water, then dried (MgSO₄) and stripped in vacuo gives the compound, which can be purified by the method outlined in B2 above.

EXAMPLE 14

B7. Benzhydryl 3-formyl-7-(2-thienylacetamido)-2-cephem-4-carboxylate (33)

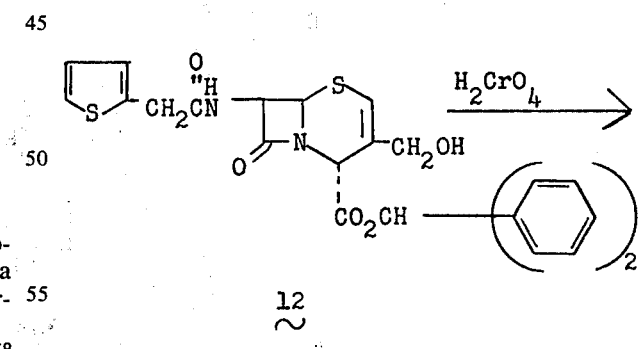

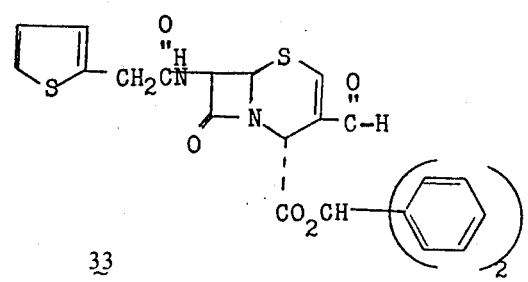

This compound is prepared according to German Offenlegungschrift 2,103,014 as follows: A solution of 1.04 g of the hydroxymethyl compound 12 in 50 ml of acetone at 0° is treated with 0.6 ml of 8N CrO₃ in sulfuric acid and stirred at 0° for 20 minutes. The mixture is poured into 150 ml of water and extracted with ethyl acetate. The ethyl acetate layer is washed with water and then dried (MgSO₄) and stripped in vacuo. The product is chromatographed on silica gel with chloroform to yield benzhydryl 3-formyl-6-(2-thienylacetamido)-2-cephem-4-carboxylate, mp 141-142.5°d.

B8. Benzhydryl
3-Difluoromethyl-7-(2-thienylacetamido)-2-cephem-4-carbonxylate (34)

To a solution of 1.56 g of benzhydryl 3-formyl-7-(2-thienylacetamido)-2-cephem-4-carboxylate in 25 ml of CH₂Cl₂ at 27° is added 0.483 g of diethylaminosulfur trifluoride and the mixture is stirred at 27° for 1.5 hour, then poured into water. The CH₂Cl₂ layer is dried (MgSO₄) and evaporated in vacuo. The residue is chromatographed on silica with CHCl₃ to give benzhydryl 3-difluoromethyl-7-(2-thienylacetamido)-2-cephem-4-carboxylate.

EXAMPLE 15

B9. Benzhydryl
3-Difluoromethyl-7-(2-thienylacetamido)-3-cephem-4-carboxylate-1-oxide (32)

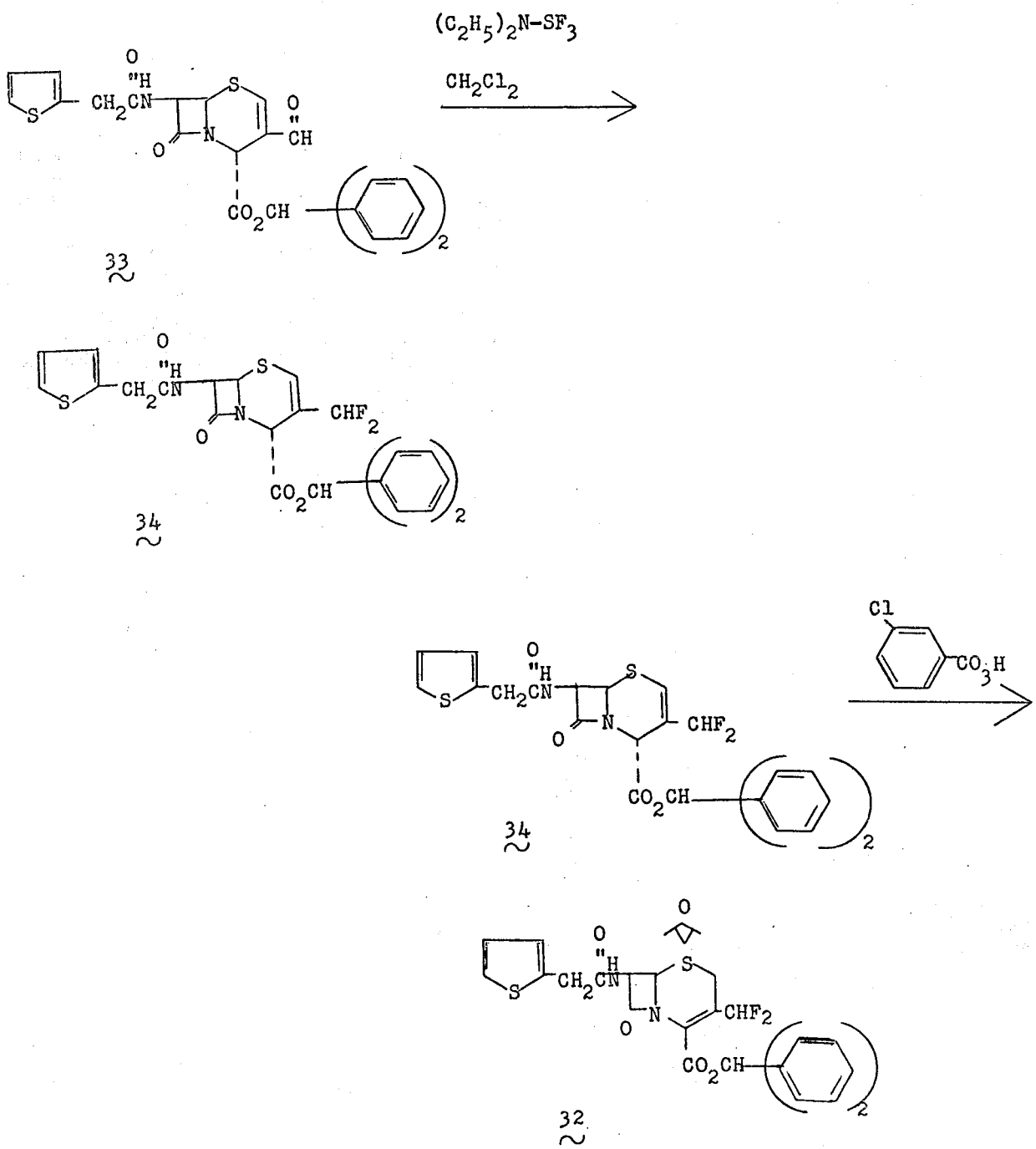

To a solution of 2.16 g of benzhydryl 3-difluoromethyl-7-(2-thienylacetamido)-2-cephem-4-carboxylate in 50 ml of CHCl₃ at 0° is added dropwise a solution of 0.860 g of m-chloroperbenzoic acid in 20 ml of CHCl₃. The mixture is stirred at 0° for 3.0 hours, then washed with 5% NaHCO₃ solution, dried (MgSO₄), and stripped in vacuo. The residue is recrystallized from methanol to give benzhydryl 3-difluoromethyl-7-(2-thienylcetamido)-3-cephem-4-carboxylate-1-oxide.

EXAMPLE 16

B10. 2,2,2-Trichloroethyl 3-Formyl-7-phenylacetamido-3-cephem-4-carboxylate-1-oxide. (35)

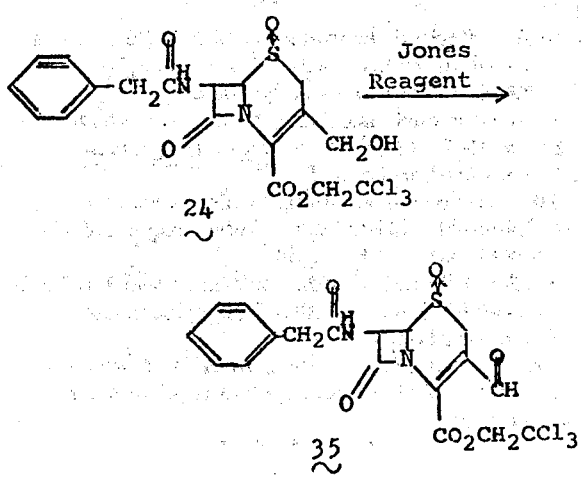

To a solution of 0.843 g (1.7 mmole) of 2,2,2-trichloroethyl 3-hydroxymethyl-7-phenylacetamido-3-cephem-4-carboxylate-1-oxide in 50 ml of acetone at 0° is added over the period of about 2 min. 0.450 ml of 8N CrO₃ in H₂SO₃ and the mixture is stirred at 0° for 5 min., then poured into a mixture of 300 ml ethyl acetate - 300 ml water and the ethyl acetate layer washed with water, dried (MgSO₄), and evaporated in vacuo. The residue when chromatographed on silica gel with CHCl₃ gives 2,2,2-trichloroethyl 3-formyl-7-phenylacetamido-3-cephem-4-carboxylate-1-oxide.

B11. 2,2,2-Trichloroethyl 3-Difluoromethyl-7-phenylacetamido-3-cephem-4-carboxylate-1-oxide (36).

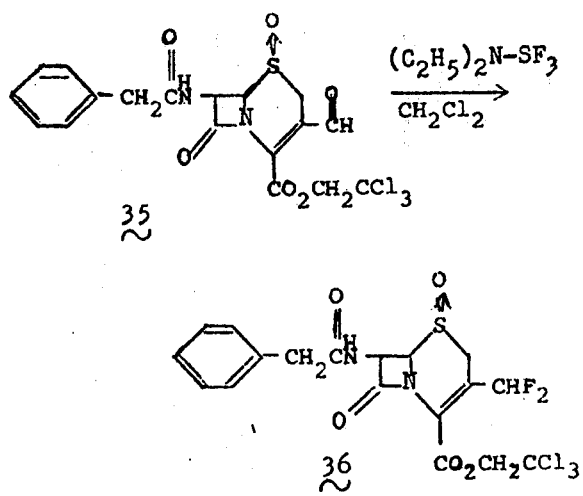

To 0.550 g of 2,2,2-trichloroethyl 3-formyl-7-phenylacetamido-3-cephem-4-carboxylate-1-oxide in 25 ml of CH₂Cl₂ at 27° is added 0.160 g of diethylaminosulfur trifluoride and the mixture is stirred at 27° for 1.0 hour, then poured into 50 ml of water. The CH₂Cl₂ layer is dried (MgSO₄), evaporated in vacuo, and the residue is chromatographed on silica with CHCl₃ to yield 2,2,2-trichloroethyl 3-difluoromethyl-7-phenylacetamido-3-cephem-4-carboxylate-1-oxide.

EXAMPLE 17

B12. 2,2,2-Trichloroethyl 3-Difluoromethyl-7-phenylacetamido-3-cephem-4-carboxylate (37)

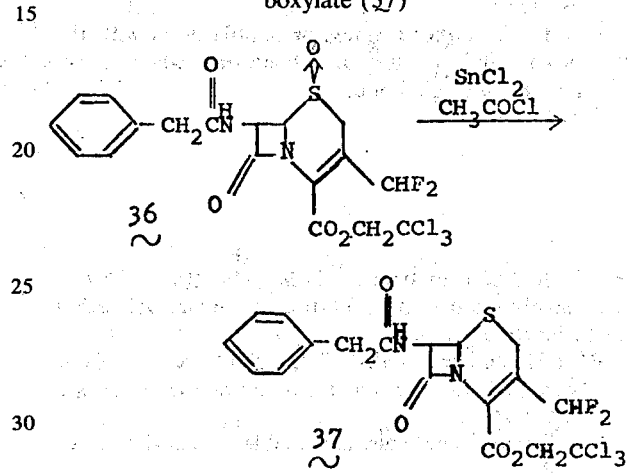

To a solution of 1.03 g (2.0 mmole) of 2,2,2-trichloroethyl 3-difluoromethyl-7-phenylacetamido-3-cepham-4-carboxylate-1-oxide in 10 ml CH₃CN and 3 ml DMF at 0° is added 0.414 g (2.2 mmole) of anhydrous SnCl₂ and 0.700 g (9 mmole) of acetyl chloride, and the resulting mixture is stirred at 0° for 1.0 hr., then at 25° for 1.0 hour, and then poured into water and extracted with ethyl acetate. The ethyl acetate layer after washing with 3% HCl solution, 5% NaHCO₃ solution, and water, and then drying (MgSO₄) and stripping in vacuo gives 2,2,2-trichloroethyl 3-difluoromethyl-7-phenylacetamido-3-cephem-4-carboxylate which can be purified by chromatography on silica gel with chloroform.

EXAMPLE 18

B13. 3-Difluoromethyl-7-phenylacetamido-3-cephem-4-carboxylic Acid (38)

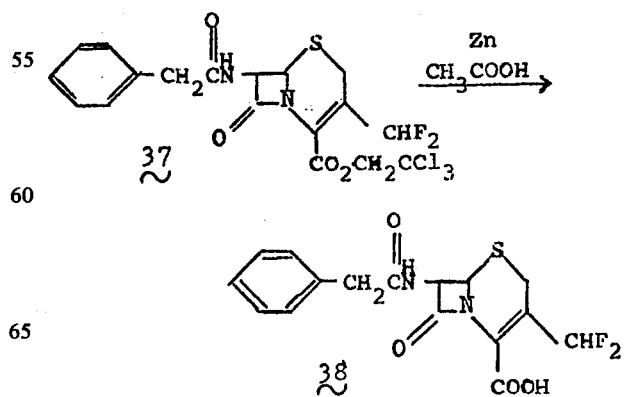

The embodiments of the invention in which an exclusive property or privilege is claimed are defined as follows:

1. A compound of the formula (1)

(1) 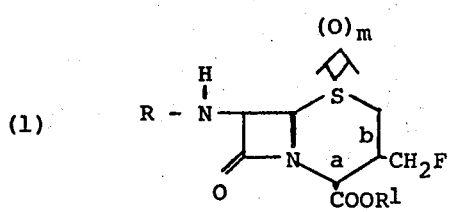

wherein
  m is zero or 1;
  a and b are either a single or double bond with the proviso that b is a double bond only when m = 0 and a is a single bond;
  R is H,

in which Q is phenylmethyl, 2-thienylmethyl, 3-[1,2,5-thiadiazolyl]methyl, 3-[2,5,6-tricyanopyrazinyl]methyl or furfurylmethyl; and
  $R^1$ is H, diphenylmethyl, 2,2,2-trichloroethyl, alkali metal, alkaline earth metal, or ammonium or amine salt; and
  2. a pharmaceutically acceptable acid addition salt of (1).

2. A compound according to claim 1 in which R is 2-thienylacetyl.

3. A compound according to claim 1 in which $R^1$ is H.

4. A compound according to claim 1 which is benzhydryl-3-fluoromethyl-7-(2-thienylacetamido)-3-cephem-4-carboxylate.

5. A compound according to claim 1 which is 3-fluoromethyl-7-(2-thienylacetamido)-3-cephem-4-carboxylic acid.

6. A compound according to claim 1 which is benzhydryl-3-fluoromethyl-7-(2-thienylacetamido)-3-cephem-4-carboxylate-1-oxide.

7. A compound according to claim 1 which is benzhydryl-7-amino-3-fluoromethyl-3-cephem-4-carboxylate.

8. A compound according to claim 1 which is benzhydryl-3-fluoromethyl-7-(3-[1,2,5-thiadiazolyl]acetamido)-3-cephem-4-carboxylate.

9. A compound according to claim 1 which is 3-fluoromethyl-7-(3-[1,2,5-thiadiazolyl]acetamido)-3-cephem-4-carboxylic acid.

10. A compound according to claim 1 which is 2,2,2-trichloroethyl-3-fluoromethyl-7-phenylacetamido-3-cephem-4-carboxylate-1-oxide.

11. A compound according to claim 1 which is 2,2,2-trichloroethyl-3-fluoromethyl-7-phenylacetamido-3-cephem-4-carboxylate.

12. A compound according to claim 1 which is 3-fluoromethyl-7-phenylacetamido-3-cephem-4-carboxylic acid.

* * * * *